US009700686B2

(12) United States Patent
Gavini et al.

(10) Patent No.: US 9,700,686 B2
(45) Date of Patent: Jul. 11, 2017

(54) FLUID DELIVERY DEVICES AND METHODS

(71) Applicant: Novopyxis, Inc., Cambridge, MA (US)

(72) Inventors: Madhavi Gavini, Cambridge, MA (US); Rathi L. Srinivas, Cambridge, MA (US); Raja Srinivas, Cambridge, MA (US)

(73) Assignee: Novopyxis, Inc., Cambridge, MA (US)

( * ) Notice: Subject to any disclaimer, the term of this patent is extended or adjusted under 35 U.S.C. 154(b) by 0 days.

(21) Appl. No.: 15/173,142

(22) Filed: Jun. 3, 2016

(65) Prior Publication Data
US 2016/0354559 A1 Dec. 8, 2016

Related U.S. Application Data

(60) Provisional application No. 62/170,216, filed on Jun. 3, 2015.

(51) Int. Cl.
A61M 11/00 (2006.01)
A61M 11/02 (2006.01)
(Continued)

(52) U.S. Cl.
CPC ........... *A61M 11/007* (2014.02); *A45D 34/00* (2013.01); *A61F 9/0008* (2013.01);
(Continued)

(58) Field of Classification Search
CPC .... A61M 2210/04; A61M 5/30; A61M 5/007; A61M 11/005; A61M 11/002;
(Continued)

(56) References Cited

U.S. PATENT DOCUMENTS 4,268,460 A * 5/1981 Boiarski ................ A61M 11/06
128/200.16
5,485,828 A 1/1996 Hauser
(Continued)

FOREIGN PATENT DOCUMENTS

DE 1103522 B 3/1961
DE 3019943 A1 12/1981
(Continued)

OTHER PUBLICATIONS

Oberli et al., Ultrasound-enhanced transdermal delivery: recent advances and future challenges. Ther Deliv. Jul. 2014;5 (7):843-57.

*Primary Examiner* — Peter S Vasat
(74) *Attorney, Agent, or Firm* — Mintz Levin Cohn Ferris Glovsky and Popeo, P.C.

(57) ABSTRACT

Methods, systems, and devices are provided for generating a mist. In one embodiment, a fluid delivery device is provided that includes a housing, a fluid vaporizer disposed within the housing and configured to receive fluid and to produce an aerosol mist of liquid particles from the fluid, and a pump configured to accelerate the aerosol mist produced by the fluid vaporizer. Methods are provided for producing a mist, and the methods can include delivering a fluid to a fluid vaporizer that generates a first mist. The fluid vaporizer delivers the mist to a pump that generates a second mist from the first mist.

25 Claims, 16 Drawing Sheets

(51) Int. Cl.
| | |
|---|---|
| A61M 5/30 | (2006.01) |
| A61M 15/00 | (2006.01) |
| A61M 31/00 | (2006.01) |
| A61M 35/00 | (2006.01) |
| B05B 11/00 | (2006.01) |
| A45D 34/00 | (2006.01) |
| A61F 9/00 | (2006.01) |
| A61K 9/00 | (2006.01) |
| A61K 9/12 | (2006.01) |
| A61K 31/546 | (2006.01) |
| A61K 31/7036 | (2006.01) |
| A61K 31/7052 | (2006.01) |
| A61K 38/12 | (2006.01) |
| B05B 15/06 | (2006.01) |
| B05B 17/06 | (2006.01) |
| A61M 21/00 | (2006.01) |

(52) U.S. Cl.
CPC .............. *A61K 9/0014* (2013.01); *A61K 9/12* (2013.01); *A61K 31/546* (2013.01); *A61K 31/7036* (2013.01); *A61K 31/7052* (2013.01); *A61K 38/12* (2013.01); *A61M 5/30* (2013.01); *A61M 11/001* (2014.02); *A61M 11/005* (2013.01); *A61M 15/0085* (2013.01); *A61M 31/00* (2013.01); *A61M 35/00* (2013.01); *B05B 11/00* (2013.01); *B05B 15/061* (2013.01); *B05B 17/0676* (2013.01); *A45D 2200/057* (2013.01); *A61M 15/0003* (2014.02); *A61M 2021/0066* (2013.01); *A61M 2021/0072* (2013.01); *A61M 2205/07* (2013.01); *A61M 2205/13* (2013.01); *A61M 2205/276* (2013.01); *A61M 2205/332* (2013.01); *A61M 2205/3561* (2013.01); *A61M 2205/3569* (2013.01); *A61M 2205/3592* (2013.01); *A61M 2205/36* (2013.01); *A61M 2205/50* (2013.01); *A61M 2205/6018* (2013.01); *A61M 2205/8206* (2013.01); *A61M 2205/8237* (2013.01); *A61M 2206/20* (2013.01); *A61M 2209/086* (2013.01); *A61M 2210/04* (2013.01); *A61M 2210/0625* (2013.01); *A61M 2210/0662* (2013.01); *A61M 2210/1067* (2013.01); *A61M 2210/1475* (2013.01); *A61M 2230/63* (2013.01)

(58) Field of Classification Search
CPC .. A61M 11/003; B05B 7/1468; B05B 7/2489; B05B 17/0607; B05B 17/0646; B05B 11/30; B05B 1/26; B05B 1/34; A61B 2218/003
See application file for complete search history.

(56) References Cited

U.S. PATENT DOCUMENTS

| | | | |
|---|---|---|---|
| 9,056,324 B2 | 6/2015 | Fedorov | |
| 9,061,295 B2 | 6/2015 | Fedorov | |
| 2003/0140921 A1* | 7/2003 | Smith | A61J 1/065 128/200.14 |
| 2004/0260234 A1 | 12/2004 | Srinivasan et al. | |
| 2005/0228338 A1 | 10/2005 | Greenberg | |
| 2007/0055200 A1 | 3/2007 | Gilbert | |
| 2008/0054099 A1 | 3/2008 | Giroux et al. | |
| 2008/0169575 A1* | 7/2008 | Chen | F24F 5/0035 261/28 |
| 2009/0223513 A1* | 9/2009 | Papania | A61M 15/0065 128/200.16 |
| 2009/0318852 A1 | 12/2009 | Reed et al. | |
| 2013/0079733 A1* | 3/2013 | Burt | B05B 7/0012 604/290 |
| 2015/0014433 A1* | 1/2015 | Albert | B05B 7/066 239/102.2 |
| 2015/0014434 A1 | 1/2015 | Fedorov | |
| 2015/0097047 A1 | 4/2015 | Hu et al. | |

FOREIGN PATENT DOCUMENTS

| | | |
|---|---|---|
| DE | 3202597 A1 | 8/1983 |
| EP | 1818070 A2 | 8/2007 |
| JP | 2008168222 A | 7/2008 |
| WO | 2006006963 A2 | 1/2006 |
| WO | 2009013954 A1 | 1/2009 |
| WO | 2011061480 A1 | 5/2011 |

* cited by examiner

CROSS SECTION OF CHICKEN TISSUE
1cm DEPTH

AEROSOL — NO BLUE DYE VISIBLE

DEVICE — BLUE DYE VISIBLE

CEFTAROLINE, A 762DA ANTIBIOTIC FOR MRSA

FLUID DELIVERY DEVICES AND METHODS

CROSS REFERENCE TO RELATED APPLICATIONS

The present application claims priority to U.S. Provisional Patent Application No. 62/170,216, filed Jun. 3, 2015 and entitled "Fluid Delivery Devices and Methods," which is incorporated by reference in its entirety.

FIELD

Methods, systems, and devices are provided for delivering fluid to a surface containing cells.

BACKGROUND

Fluid delivery for localized delivery of molecules into tissues in a patient and transfection and/or introduction of materials into cells suffers from limitations of existing technologies. Delivering a fluid containing an agent to a localized spot within a patient is an important fluid delivery method for a variety of treatments, such as localized delivery of antibiotics, the treatment of diabetes, various genetic disorders, novel cancer treatments, and an expanding number of cosmetic uses. Specifically, transdermal delivery refers to delivering an agent by crossing a skin of the patient. As an example, transdermal delivery of antibiotics is preferably used in treating skin and soft tissue infections. This localized treatment can be especially important where traditional oral and/or intravenous delivery mechanisms are ineffective or less-than-ideal, or a combination of different delivery devices and methods can be used together to improve delivery results. It can also be important to deliver large molecules such as plasmids or vectors into cells over a localized surface, such as into skin cells.

Using a transdermal delivery approach for localized delivery is superior to hypodermic injections because hypodermic injections can be painful, risk infection via needle reuse or misuse, and can create medical waste.

There are several approaches to transdermal delivery, each of which range in terms of effectiveness for particular applications. Transdermal patches can be applied directly to the outer layer of the skin. However, the patches only penetrate through the stratum corneum, which is only about 10 μm thick. Thus the vast majority of molecules cannot cross the stratum corneum. There is also a risk of infection due to the requirement for direct contact with the skin.

Other approaches involve the use chemical enhancers and iontophoresis. Another approach is the use of ultrasound. Electroporation, or the use of voltage pulses, has also been used for transdermal delivery. Microneedles are also used in transdermal delivery, consisting of very short needles that physically pierce the stratum corneum and thereby allow small molecules to cross the barrier of a patient's skin. Microneedles increase skin permeability by creating micron-sized holes in the skin layer to create an opening for small molecules. However, all of these approaches can irritate the skin and many are too expensive to be of wide-spread use.

The current approaches to delivery of an agent are therefore inadequate and there remains a need for devices and methods for providing local delivery of an agent to tissue in a manner that can be easily administered, and/or that causes as little skin irritation and pain as possible.

Methods of fluid delivery for transfecting cells with a range of molecules including but not limited to DNA, RNA, plasmids, and proteins also suffer from current limitations. Delivery into cells is crucial for gene therapy and for use with CRISPR editing methods. Standard approaches for introducing materials into cells include: electroporation in which voltage is applied across the cell membrane to create pores that allow material to enter, use of chemical transfection reagents (such as Lipofectamine) that use liposomal delivery, microinjection, and use of cell penetrating peptides (CPP).

Most of these methods lead to significant cell death because of shock to the cell. In several cases, electroporation or chemical transfection is not compatible with several subsets of cells that are sensitive to their surrounding environments and are prone to cell death via standard methods of delivery. Efficient and non-toxic delivery is especially a challenge for cells that are not in high abundance (such as populations of T-cells that are isolated from a patient and transected with genes for CAR-T therapy). In these cases, methods with high toxicity will severely impact the efficacy of treatment with genetically altered cells.

Large molecules cannot be locally delivered into cells in patients using any of these methods. Often, viruses are used to transfect genes into patient cells, but this approach has limitations and can lead to several off-target effects.

There is a need for gentler, more effective, localized approaches to deliver a variety of types of molecules into cell lines for use in a variety of settings, for example as a research tool or in therapeutic settings. The present disclosure thus provides methods, systems, and devices for more effective delivery of fluid.

SUMMARY

Various methods and devices are provided for use of a fluid delivery device.

In one embodiment, a fluid delivery device is provided that includes a housing. A fluid vaporizer is disposed within the housing and is configured to receive fluid and to produce an aerosol mist of liquid particles from the fluid. A pump is also provided that is configured to accelerate the aerosol mist produced by the fluid vaporizer.

The fluid delivery device can vary in a number of ways. For example, the fluid vaporizer can comprise a piezoelectric transducer. In another example, the pump can have an inlet port positioned to disrupt a flow path of the aerosol mist produced by the fluid vaporizer such that the aerosol mist can be drawn into the pump through the inlet port. The pump can also have an outlet port for expelling the aerosol mist therefrom. In still another example, the housing can have an inlet formed therein for allowing a fluid to be delivered into the fluid-retaining reservoir. In another example, the pump can be configured to reduce a size of the liquid particles produced by the fluid vaporizer. In still another example, the pump can be configured to reduce a size on average of the liquid particles produced by the fluid vaporizer by a factor of about 10. In one embodiment, the housing can have a fluid-retaining reservoir, and the fluid vaporizer can be configured to receive fluid from the reservoir. In another embodiment, the fluid vaporizer and the pump can be configured to generate an aerosol mist that can pass into up to 1 cm of tissue when an outlet on the housing through which the aerosol mist passes is positioned about 1 cm away from a tissue surface. Tissue or a tissue surface can include cells or a surface containing cells. In another example, the aerosol mist can be configured to pass into the tissue or the cells on a timescale of between 1 microsecond and 600 seconds. In still another example, the pump can be configured to accelerate the aerosol mist such that the aerosol mist emerging from the fluid vaporizer is focused over a given delivery radius.

In one embodiment, the device can be configured to deliver fluid into tissue without excising cells of the tissue. In one example, the device can include a stopper removably disposed within the inlet in the housing. In another example, the housing can have an outlet formed therein and positioned such that the fluid vaporizer can eject the aerosol mist from the housing through the outlet. In still another example, the pump can be configured to draw in and accelerate the aerosol mist after the aerosol mist passes through the outlet in the housing. In yet another example, the pump can include a fluid inlet port and a fluid outlet port, the fluid inlet and outlet ports being positioned adjacent to the outlet in the housing. In still another example, the fluid inlet and outlet ports of the pump can extend substantially parallel to one another and can extend transverse to a central longitudinal axis of the outlet in the housing. In another example, the fluid vaporizer can be disposed between a reservoir and an outlet formed in the housing.

In one embodiment, the pump can comprise a diaphragm pump. In another embodiment, the pump can include an axial fan. In still another embodiment, the housing can include an activation switch electronically coupled to the fluid vaporizer and/or the pump. In yet another embodiment, the activation switch can be configured to simultaneously activate the fluid vaporizer and the pump. In still another embodiment, the housing can include a handle portion configured to be grasped by a user and a body portion having the fluid vaporizer and the pump disposed therein. In one example, the housing can include a power source for providing power to the fluid vaporizer and the pump. In another example, the power source can comprise a battery. In still another example, the device can include a cartridge removably matable to the housing and configured to deliver fluid to the housing. In yet another example, the cartridge can be configured to provide a dosage instruction and/or timing instructions to the device including a selected pump-speed of the pump and a selected frequency of vibration of the fluid vaporizer for the fluid. In still another example, the device can be configured to be inoperable unless the cartridge is mated to the housing. In yet another example, the housing can include an activation switch that is electronically coupled to the fluid vaporizer and the pump and that can be configured to simultaneously activate the fluid vaporizer and the pump according to the dosage instruction of the cartridge.

In another example, the device can include a controller disposed on the housing and configured to alter a frequency of the fluid vaporizer and a pump-speed of the pump and/or duration of device operation. In another example, the device can include a sensor disposed on the housing and configured to determine a distance from the device to a skin of a patient. In yet another example, the device can include a sensor electronically coupled to a gyroscope and an accelerometer disposed in the housing and configured to determine an orientation of the device. In still another example, the device can include a fluid wherein the fluid includes a drug having a molecular weight of at least about 500 Daltons. In yet another example, the device can include a fluid that includes a drug having a molecular weight of up to about 800 Daltons. In still yet another example, the device can include a fluid that includes a drug having a molecular weight of at least about 800 Daltons. In one embodiment, the device can include a cosmetically acceptable topical carrier. In another embodiment, the device can include a fluid that includes an oil-water emulsion. In still another embodiment, the device can include a fluid that includes at least one of a DNA, protein, virus, phage, bacteria, RNA, mRNA, miRNA, aptamer, stabilized RNA, iRNA, siRNA, chemicals, small molecules, and a plasmid. In yet another embodiment, the device can include a vaporized fluid configured for at least one of inhalation, oral delivery, ocular delivery, intra-aural delivery, rectal delivery, and vaginal delivery. In yet another embodiment, the device can include a vaporized fluid that can be configured for at least one of intra-cellular, intra-nuclear, and intra-tissue delivery. In another embodiment, the device can include a vaporized fluid that is configured for at least one of intra-plant delivery, polymeric delivery, and protein-structure delivery.

In another aspect, a fluid delivery device is provided that includes a housing. A fluid vaporizer is disposed within the housing and is configured to receive fluid and to produce an aerosol mist of individual non-coalescing droplets from the fluid by creating an inertia-dominated fluid regime in the fluid. The device also includes an acceleration system disposed within the housing and configured to accelerate the aerosol mist.

The device can vary in a number of ways. For example, the device can be configured to eject a vaporized fluid having a Weber number that is equal to or greater than 1, or that is in the range of about 1 to 100, and more preferably that is in the range of about 10 to 50.

In another aspect, a fluid delivery device is provided with a housing with a fluid-retaining reservoir in the housing. A piezoelectric transducer is disposed within the housing and is configured to receive fluid from the reservoir and to produce an aerosol mist of liquid particles from the fluid. The housing has an outlet formed therein that is positioned such that the piezoelectric transducer can eject the aerosol mist from the housing through the outlet. A pump has an inlet and an outlet that are positioned adjacent to the outlet of the housing. The inlet port is configured to draw into the pump the aerosol mist ejected from the outlet in the housing, and the outlet port is configured to expel the aerosol mist therefrom into a path of the aerosol mist ejected from the housing by the piezoelectric transducer.

In another aspect, a method of producing a mist is provided that includes delivering a fluid to a fluid vaporizer that generates a first mist. The fluid vaporizer delivers the mist to a pump that generates a second mist from the first mist.

The method of producing a mist can vary in numerous ways. For example, the second mist can have a reduced size relative to the first mist. In another example, the fluid vaporizer can comprise a piezoelectric transducer. In still another example, delivering a fluid to the fluid vaporizer can comprise delivering a fluid to a fluid-retaining reservoir that is in fluid communication with the fluid vaporizer. In yet another example, the fluid can be delivered to the fluid vaporizer using a removable cartridge. In still another example, a flow path of the first mist produced by the fluid vaporizer can be disrupted by an inlet port and an outlet port on the pump. In one embodiment, the second mist can be ejected from the pump into a flow path of the first mist produced by the fluid vaporizer. In still another embodiment, the first mist and the second mist can be delivered to a skin surface of a patient. In another embodiment, the first mist and the second mist can be delivered to cells in a plate or well. In yet a further embodiment, the method can include activating an activation switch electronically coupled to the fluid vaporizer and to the pump to activate the fluid vaporizer and the pump.

In one example, the method can further include positioning an outlet of each of the pump and the fluid vaporizer adjacent to a surface, such as a tissue or cells, and a distance from the pump and the fluid vaporizer to a skin of a patient can be detected by a sensor. In still another example, the fluid can comprise a drug having a molecular weight of at least about 500 Daltons. In another example, the fluid can comprise a drug having a molecular weight of up to about 800 Daltons. In still another example, the fluid can comprise a drug having a molecular weight of at least about 800 Daltons. In yet another example, the fluid can include cosmetically acceptable topical carriers. In still yet another example, the fluid can include oil-water emulsions. In one embodiment, the fluid can include at least one of a DNA, a protein, a virus, a phage, bacteria, RNA, mRNA, miRNA, an aptamer, stabilized RNA, iRNA, siRNA, and a plasmid suspended in the fluid. In another embodiment, activating a switch on the housing can generate the first mist and the second mist configured for at least one of inhalation, oral delivery, ocular delivery, intra-aural delivery, rectal delivery, and vaginal delivery. In still another embodiment, the pump can reduce a size on average of particles of the first mist produced by the fluid vaporizer by a factor of about 10. In yet another embodiment, the method can include directing a flow of the first mist and a flow of the second mist at a site selected from an eye, an ear, a wound, a burn, an infection, a surgical site, isolated cells, and a plurality of cells in a section of tissue.

In another aspect, a method for creating a mist is provide that includes introducing an aerosol in a housing and activating a switch on the housing such that the housing expels a mist of the aerosol from a first outlet in the housing. The mist is then drawn into an inlet of a pump in the housing and is expelled by a second outlet of the pump into a path of the mist from the first outlet in the housing such that droplets of the mist collide and break apart.

In another aspect, a method for creating a mist is provide that includes introducing an aerosol into a housing and activating a switch on the housing such that the housing expels a mist of the aerosol from a first outlet in the housing. The mist is then accelerated by a pump within the housing using an exhaust that emerges from the pump. Droplets in the mist collide and break apart and gain acceleration.

BRIEF DESCRIPTION OF DRAWINGS

The invention will be more fully understood from the following detailed description taken in conjunction with the accompanying drawings, in which:

FIG. 15 is an image showing tissue penetration by an aerosol and using a fluid delivery device as disclosed herein;

FIG. 16 is a graph showing molecular size capabilities with a topical application as compared to a fluid delivery device as disclosed herein;

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

In general, methods and devices are provided for generating a fluid mist stream that is capable of penetrating into tissue or into cells while minimizing any tissue irritation and/or pain and without the need for direct contact between the device and the tissue or the cells. In an exemplary embodiment, the methods and devices are used for transdermal fluid delivery, however the methods and devices can be utilized in surgical approaches to apply a fluid to tissue intracorporeally.

In an exemplary embodiment, a fluid delivery device is provided having a housing with a fluid-retaining reservoir, a piezoelectric transducer disposed within the housing and configured to receive fluid from the reservoir and to produce an aerosol mist of deformable liquid particles from the fluid, and a pump configured to pump the aerosol mist produced by the piezoelectric transducer therethrough. A handle of the housing can have a trigger that can be activated to cause fluid flow through the device. The handle can be sized to allow a user to grasp the handle in one hand while simultaneously operating the trigger with a finger on that same hand. A power source, such as a replaceable battery, may be located in the interior of the handle, or the handle can include a plug or cord, or any combination of the two, for connecting to an external power source. The power source can also be located in the body of the device. A body of the housing can have an inlet and an outlet. The inlet can be configured to receive fluid from a fluid supply device, such as a syringe or cartridge. The inlet may be upstream of the reservoir and the piezoelectric transducer. The outlet can be configured to provide a passage through which fluid can exit the device. The outlet can be positioned adjacent to the pump. In an exemplary embodiment, fluid expelled from the outlet can be drawn into the pump and then expelled from the pump. The particular arrangement of the outlet and the pump has been found to create a fluid stream that is effect to penetrate into tissue without excising the tissue cells or across the cell membrane for entry into cells. Due to the deep penetration, the fluid will remain within the tissue for longer periods as compared to prior art methods. The particular arrangement has also been found to allow for the delivery of molecules having a much larger size as compared to prior art fluid delivery devices. The particular arrangement is additionally capable of delivering large molecules (such as plasmids) into cells.

FIGS. 1-4 illustrate one embodiment of a device 1 that generally includes a housing 10 having a handle 11 and a body 12 extending from the handle. The illustrated housing 10 is formed from two pieces, a top 10*t* and a bottom 10*b* (as seen in FIG. 4), that mate together to form the housing 10 and that define an interior cavity within the housing. The housing 10 includes a handle portion 11 for grasping and a body portion 12 extending from the handle 11. The housing 10 can be made of any rigid material, such as plastic or metal. The illustrated housing 10 is shown seated within a cradle 15. While the cradle 15 is illustrated as a receiving base into which the housing 10 is placed, one skilled in the art will appreciate that the cradle 15 can be any structure that is capable of seating the housing 10. For example, the cradle 15 can be a vertical structure, a structure attached to other devices or equipment, and/or a structure securable to a user (such as a structure securable to a belt). The cradle 15 may also include other features, such as features for securing the housing 10 in place. These can include, for instance, clips, clamps, magnetic holdings, straps, or any other securing mechanism operable with the housing 10. The cradle 15 can further include charging or power mechanisms operable to provide power to the housing 10 or to a power source within the housing 10. For example, the cradle 15 can include cables, wires, coils, or any other mechanism for providing power or charging to the device. The cradle 15 can be made of any rigid or soft material, such as plastic, metal, or cloth capable of retaining the housing 10. In other embodiments, the housing can be designed to be free-standing without the use of a cradle.

The handle 11 of the illustrated housing 10 has a proximal end 11*p* and a distal end 11*d*. While the handle 11 is generally cylindrical and elongate in shape, the handle 11 can have any shape or size that would allow a user to grasp the handle in one hand, such as a pistol grip, a pencil grip, a scissor, grip, or any other configuration. As further shown, the handle 11 includes a trigger 13. The illustrated trigger 13 is located on the housing bottom surface of the bottom 10*b*, however the trigger 13 can be positioned at any location on the device 1, for example on the top or bottom of the handle 11 or the top or bottom of the body 12, or on any side surface thereof. Activation of the trigger 13 is effective to activate a pump 40 and a piezoelectric transducer 30 within the house, while release of the trigger 13 will terminate use of the pump 40 and the piezoelectric transducer 30. While the illustrated trigger 13 activates the pump 40 and piezoelectric transducer 30, one skilled in the art will appreciate that activation of the trigger 13 may cause a variety of different functions and/or processes of the device to activate. For example, activation of the trigger can cause activation of the pump and/or the piezoelectric transducer at selectable pump-speeds and/or frequencies of vibration and voltages, respectively. The illustrated trigger 13 includes a button cover 13*c*, a button bracket 13*b*, and a switch 13*s* electrically coupled to a circuit board 50 within housing 10 (as seen in FIGS. 4 and 6). However, the trigger 13 may be any type of switch capable of being electrically coupled to the circuit board 50, such as a dial, a slide, a lever, a knob, a button, a touch screen, or a touch panel. The trigger 13 can also be any type of sensor, such as a distance sensor or a pressure sensor that can be automatically activating if the device is within a certain distance or pressed against a barrier (for example a patient's skin).

Within the proximal end 11*p* of the handle 11, a power source 17 is electrically coupled to the circuit board 50 (as seen in FIG. 4). The power source 17 is shown as a replaceable battery 17*b* with a battery connector 17*c* (as seen in FIG. 6). However, the power source 17 may be anything that is configured to supply power to the device. For example, the power source 17 may be a rechargeable battery or a cord extending from the proximal end 11*p* of the handle and configured to plug into an outlet or power source. The power source 17 may be replaceable by a user. For example, the top and bottom 10*t*, 10*b* of the housing 10 can be separable as shown in FIG. 4, or the proximal end 11*p* of the handle can include a removable battery cover (not shown) to provide access to the power source 17.

Figure 1:
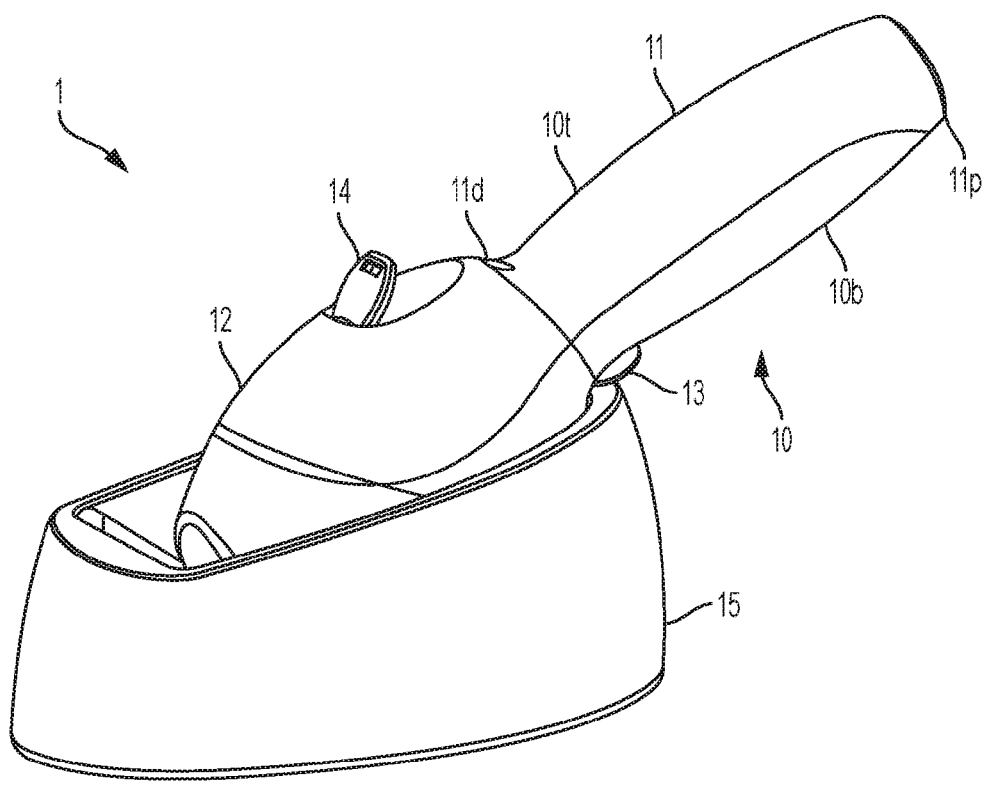
FIG. 1 is a side perspective view of one embodiment of a fluid deliver device and a cradle.
Figure 2:
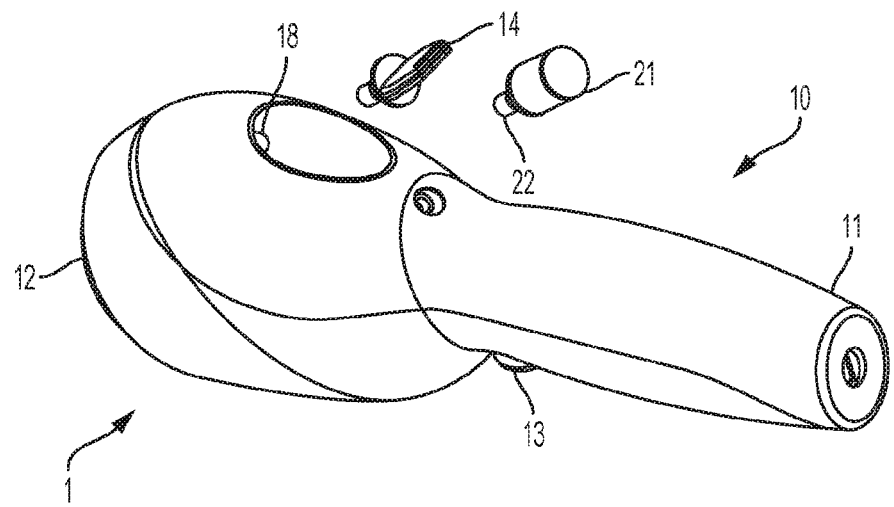
FIG. 2 is a side perspective, partially exploded view of the fluid delivery device of FIG. 1.
Figure 3:
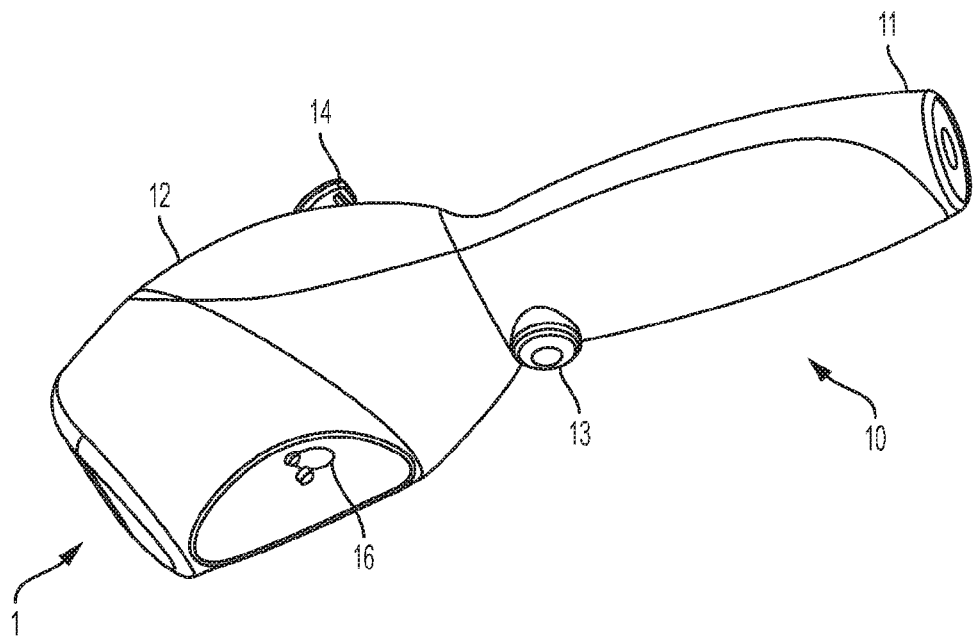
FIG. 3 is another side perspective view of the fluid delivery device of FIG. 1.

As shown in FIG. 2, the body 12 of the housing has an inlet 18 for allowing fluid to be delivered into the housing 10. The illustrated inlet 18 has a stopper 14 seated therein, with the stopper removed the inlet 18 can be configured to receive a cartridge 21. The inlet 18 receives fluid added to the device, and the fluid may be expelled from an outlet 16 in the housing 10, as seen in FIG. 3. The illustrated inlet 18 is shaped as a cylindrical channel with a diameter of approximately 0.1 mm to approximately 10 cm. For example, the diameter can be approximately 1.5 mm. However, one skilled in the art will appreciate that the inlet 18 may be sized and/or shaped in any form necessary to receive fluid, as well as to seat the stopper 14 and/or the cartridge 21. Other shapes include, by way of non-limiting example, a cuboid receiving channel, a receiving slot, or a receiving tray. The illustrated outlet 16 is also shaped as a cylindrical channel with a diameter of approximately 0.1 mm to approximately 10 cm. For example, the diameter can be approximately 1.5 mm. Again however, one skilled in the art will appreciate that the outlet 16 may be sized and/or shaped in any form necessary to allow the expulsion of fluid. While the stopper 14 shown in FIG. 2 has a head and a plug, the stopper may also take any form that will fluidly seal the inlet 18, such as a cork, a snap-on cover, or a cap.

Figure 4:
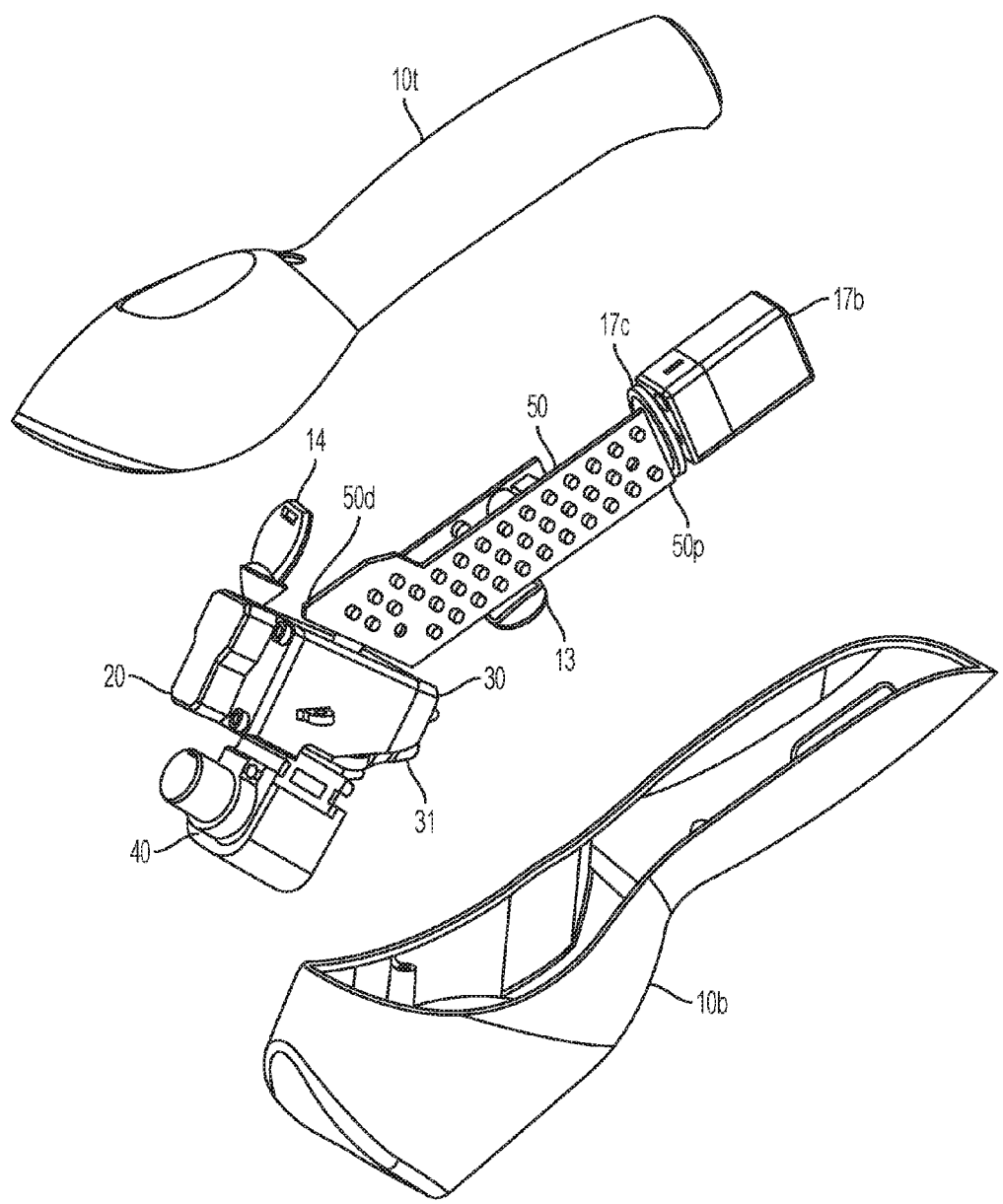
FIG. 4 is an exploded perspective view of internal and external components of the fluid delivery device of FIG. 1.

The cartridge 21 can contain fluid to be introduced into the inlet 18 and to subsequently flow downstream to a reservoir 20 (as seen in FIG. 4). The cartridge 21 may contain one type of fluid or multiple types of fluid separated by a variety of mechanisms, such as physical barriers or immiscible barriers (for example an oil phase). The cartridge 21 may also contain electrical components that may interact with the device 1. For example, the cartridge 21 can include an electrical component that may directly or wirelessly interact with the circuit board 50 and provide a signal to the circuit board 50 containing instructions and/or details on fluid type, dosage information, dispersal rates, dispersal times, or any other details related to the fluid contained within the cartridge 21. The cartridge 21 may also contain electrical, physical, or fluid components within the cartridge 21 itself that self-regulate the introduction of fluid from the cartridge 21 to the inlet 18 and/or the reservoir 20. For example, the cartridge 21 may be shaped or sized specifically to allow a particular fluid flow rate. Additionally, multiple cartridges 21 may be used together to provide a fluid combination to be introduced to the device. The illustrated cartridge 21 also has a sealed port 22 that prevents fluid flow from the cartridge 21 until insertion into the inlet 18. For example, the sealed port 22 can have a rubber or plastic seal that is punctured by the inlet 18 upon insertion. As another example, the sealed port 22 may have an electrical component that senses insertion into the inlet 18 and allows fluid flow upon activation of the device. While the cartridge 21 is illustrated as having a cylindrical shape, any shape capable of retaining fluid and being introduced into the inlet 18 can be used, such as a flexible pouch or a cuboidal structure. Additionally, the cartridge 21 can be made of any material capable of retaining fluid, for example rigid or flexible plastic or glass.

The illustrated device further includes a reservoir that is in fluid communication with the inlet. The reservoir can be a fluid retaining chamber within the housing of the device capable of receiving fluid added to the device through the inlet. The reservoir is downstream of the inlet and cartridge and upstream of a piezoelectric transducer. While a reservoir is shown, the device need not include a reservoir and instead the cartridge can form the reservoir. The cartridge can introduce fluid directly into the fluid stream of the device to the piezoelectric transducer.

In other embodiments, the device or a portion thereof can be designed for one-time use and/or can be disposable. Fluid can be introduced during use and/or immediately preceding use into the reservoir, into a part of the device containing the reservoir, and/or into port(s) and/or channel(s) leading to the fluid stream of the device.

Figure 7:
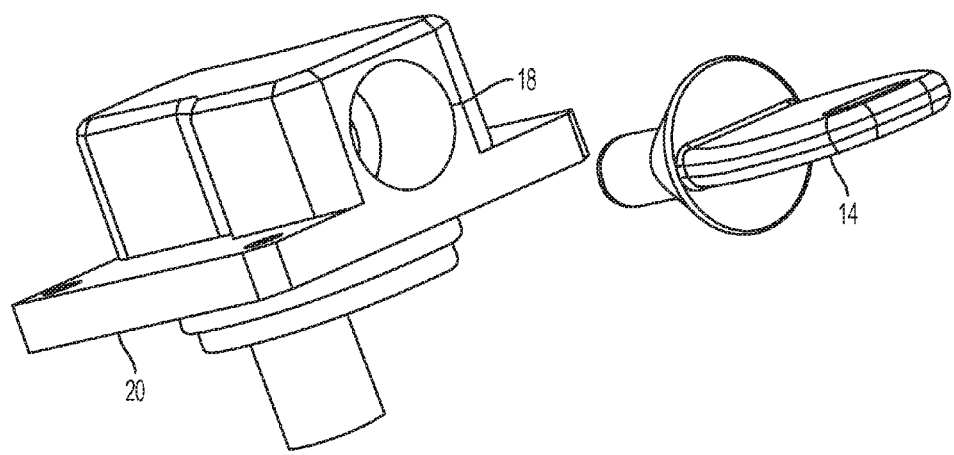
FIG. 7 is a perspective view of a stopper and reservoir of the fluid delivery device of FIG. 1.
Figure 8:
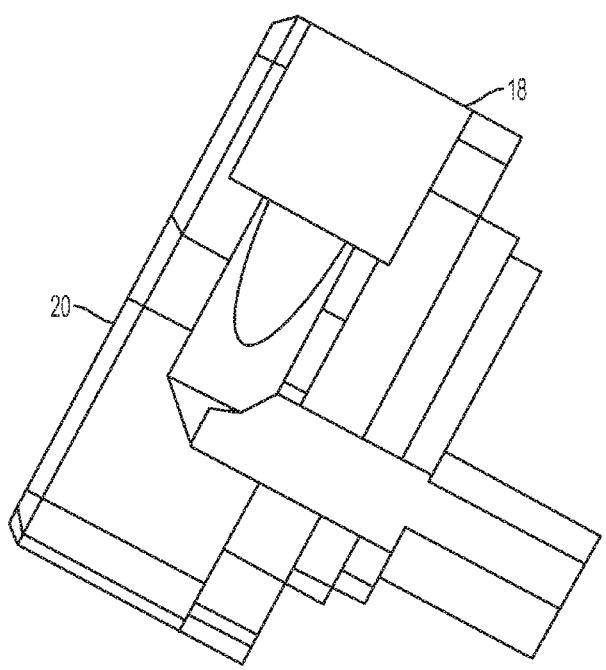
FIG. 8 is a cross-sectional view of the reservoir of FIG. 7.

As seen in FIGS. 7 and 8, the reservoir 20 is in the form of a substantially L-shaped cylindrical shaped chamber with a substantially 90° angled turn leading to the piezoelectric transducer 30. As will be appreciated by one skilled in the art, however, the reservoir 20 can have any shape and/or volume capable of retaining fluid, such as a cuboidal structure. The volume of the reservoir can also vary, and in one embodiment could be between approximately 1 μl and 500 ml.

As indicated above, the piezoelectric transducer is located downstream of the reservoir and upstream of the outlet in the housing. The piezoelectric transducer is in fluid communication with the reservoir such that fluid flows from the reservoir to the piezoelectric transducer by gravitational forces or by any other method capable of causing fluid flow, such as through use of a pump, capillary action, electromagnetic forces, vacuum suction, electrophoresis, a wick, or electro-osmotic flow. Upon contact, the piezoelectric transducer is configured to cause the fluid to separate into fluid droplets in the form of an aerosol mist of liquid particles. The fluid droplets may collide with and separate from one another within the piezoelectric transducer, further reducing droplet size. Upon expulsion from the piezoelectric transducer, the fluid droplets will flow in a transitional flow regime (between laminar and turbulent flow) or a turbulent flow regime that may cause rapid droplet coalescence and/or further droplet breakup, depending on a variety of factors such as the fluid, any exit conditions, a direction of spray, and the frequency of vibration with which the fluid droplets are generated in the piezoelectric transducer. A laminar flow regime is a flow regime characterized by flows in parallel layers with no disruption between the layers, and a turbulent flow regime is a flow regime characterized by chaotic property changes. While the device is described in connection with a piezoelectric transducer, one skilled in the art will appreciate that any component may be used that is configured to cause separation of the fluid into droplets to create an aerosol mist, such as a metal, ceramic, or conductive diaphragm.

Figure 5:
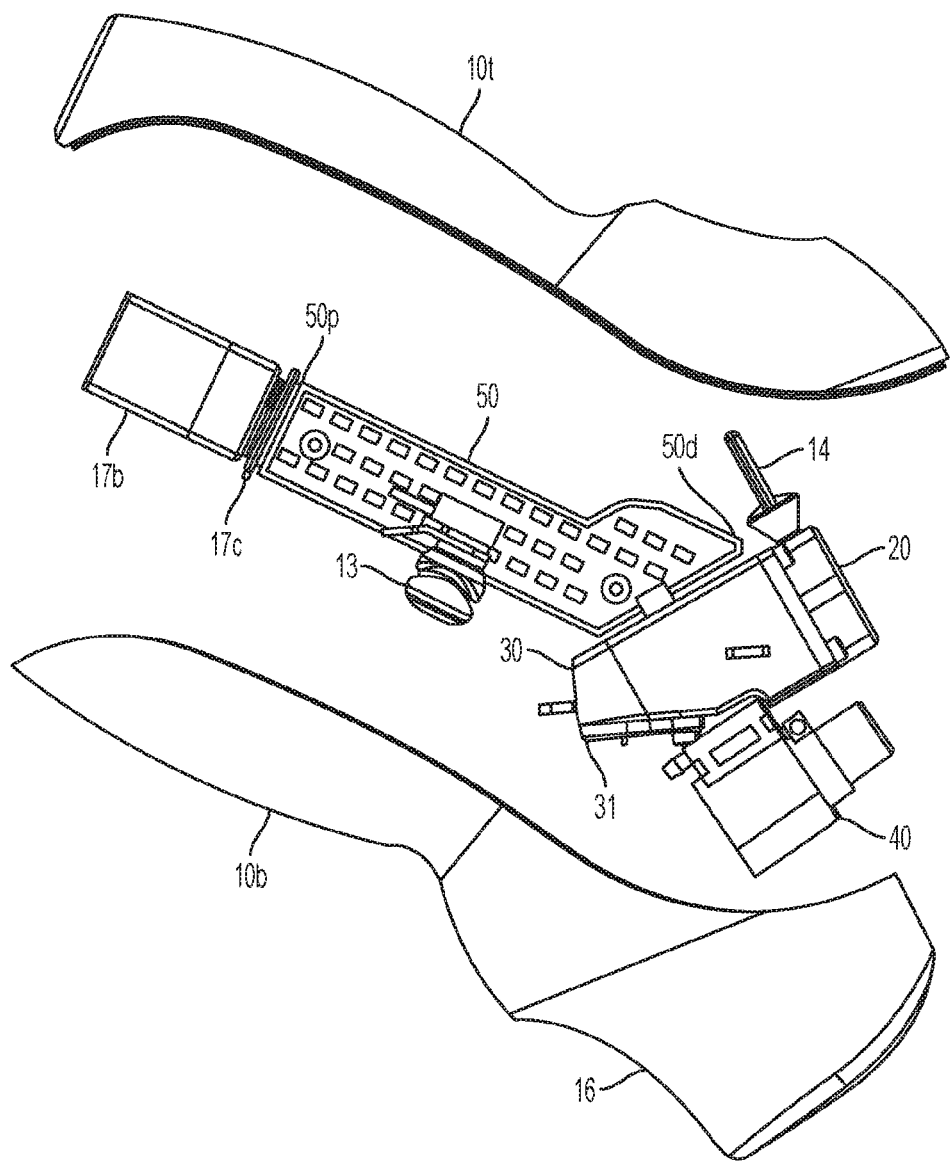
FIG. 5 is another exploded perspective view of the fluid delivery device of FIG. 4 from another side.
Figure 6:
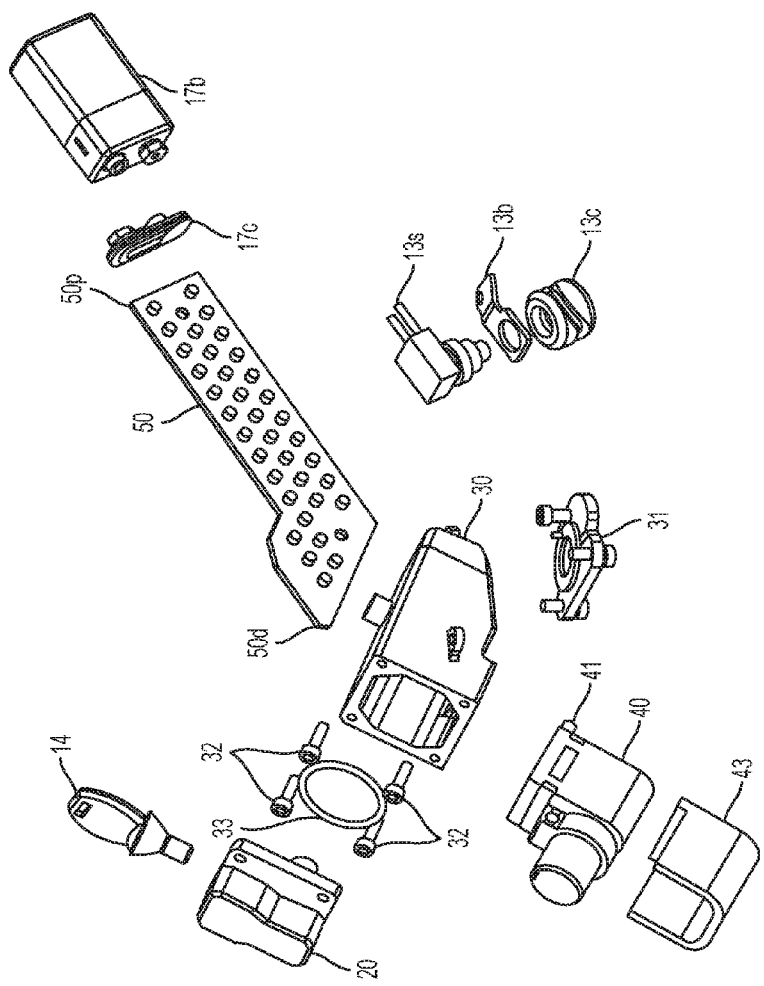
FIG. 6 is another exploded perspective view of internal components of the fluid delivery device of FIG. 1.
Figure 9:
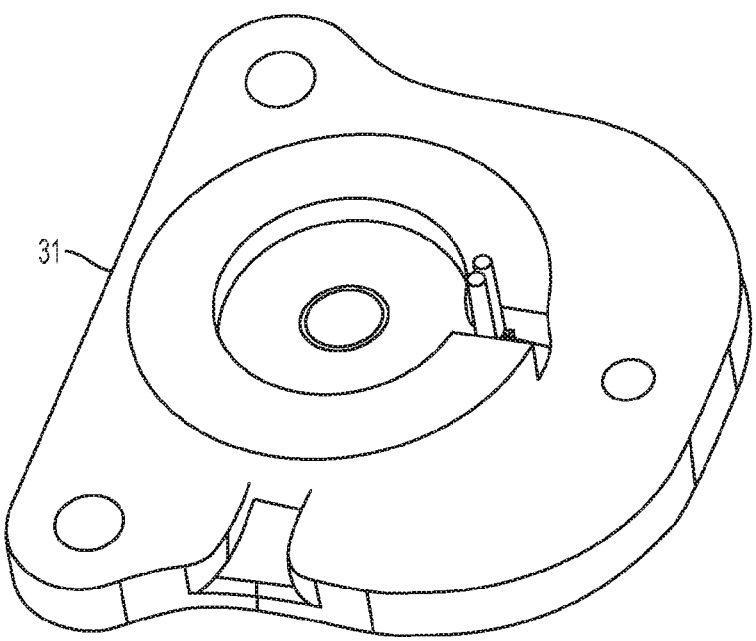
FIG. 9 is a perspective view of a top of a piezo plate of the fluid delivery device of FIG. 1.
Figure 10:
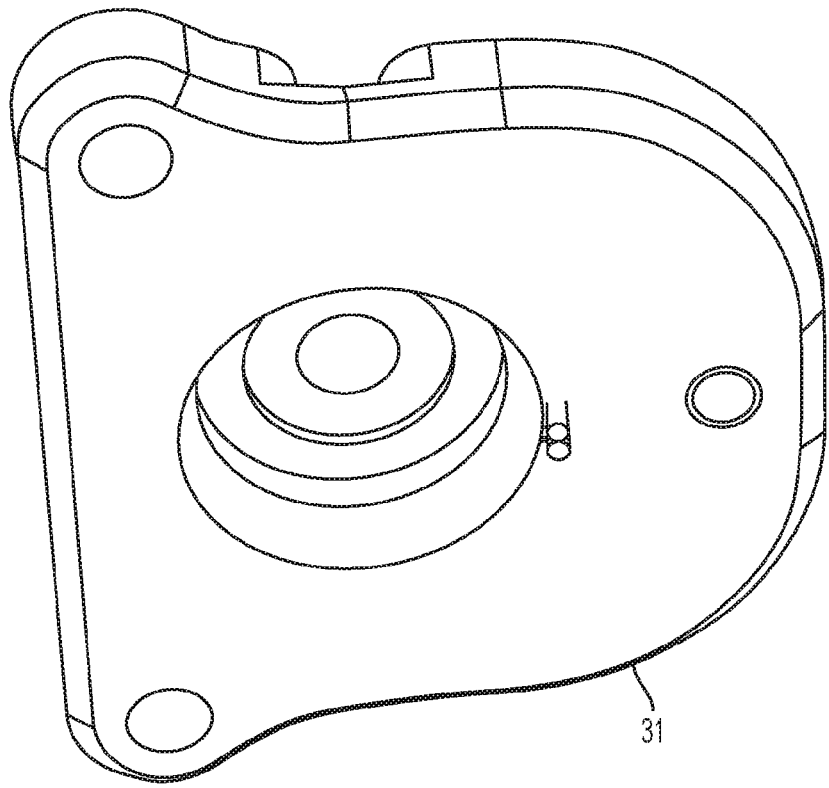
FIG. 10 is a perspective view of a bottom of the piezo plate of FIG. 9.

As illustrated in FIGS. 4-6, the piezoelectric transducer 30 is provided downstream from the reservoir 20 and upstream from the outlet 16. The piezoelectric transducer 30 is coupled to the reservoir 20 by screws 32 and passage between the two is sealed with an O-ring 33. The piezoelectric transducer 30 has a piezo plate 31, shown in more detail in FIGS. 9 and 10, that is capable of being vibrated and/or oscillated at ultrasonic frequencies to drive the separation of the fluid into droplets and to produce an aerosol mist of liquid particles from the fluid. The transducer can be manufactured, for example, by Homidics. However other transducers can be used.

The piezoelectric transducer 30 is electrically coupled to the circuit board 50 and may be activated upon activation of the trigger 13. A frequency of vibration of the piezo plate 31 may be varied to cause greater separation or less separation of the fluid. The frequency of vibration of the piezo plate can vary between 1 kHz and 10 mHz, for example. A voltage applied to the piezoelectric transducer 30 may also be varied. While the voltage can vary depending on the piezoelectric transducer, the voltage may be between −30 and 30 V, for example. The frequency of vibration and/or voltage may be varied manually or automatically. For example, the frequency and/or voltage may be varied manually through use of a controller (not shown) either directly or wirelessly coupled to the circuit board 50 and capable of sending a signal to the control board 50 or automatically based on a signal from the cartridge 21. The controller can take any form necessary to provide control over the frequency of vibration, such as a dial, a knob, a panel, or a series of buttons positioned on the housing 10 or separately from the housing 10. The controller can also include pre-set programs for controlling the device 1 or timing delivery.

The piezoelectric transducer 30 expels fluid droplets from the piezo plate 31 and through the outlet 16. A size of streams of the fluid droplets generated by the piezoelectric transducer will vary depending on the fluid and the piezoelectric transducer. For example, the streams may be microstreams with volumes ranging from approximately 1 µl to approximately 10 ml. While the piezoelectric transducer 30 herein expels fluid droplets through the outlet 16, the piezoelectric transducer 30 can also expel fluid droplets to within the housing 10. The direction and/or force of expulsion and/or size of the fluid drops may be varied, for example by varying the frequency of vibration and/or voltage.

Upon expulsion from the housing, the fluid droplets may interact with a pump or a similar component that provides the ability to pressurize and/or break up the fluid droplets by putting the droplets into a transitional flow regime or into a turbulent flow regime. The pump can be placed within the housing of the device. However, the pump may be placed anywhere as long as it can interact with the fluid droplets. The pump can have a pump inlet and a pump outlet. The pump inlet may be positioned to interact with the fluid flowing from the outlet in the housing. The pump inlet may draw the fluid droplets into the pump. An amount of the fluid in a range of about 10-90% of the fluid can be drawn into the pump, and the force of the pump can accelerate the aerosol that is not drawn into it directly via the exhaust stream. The fluid droplets can be accelerated through a pumping action of the pump and/or an exhaust stream of the pump. The pump can further increase acceleration and reduce the size of the fluid droplets by, for example, drawing droplets through the fluid path of the pump and by, for example, exhaust of the pump. For example, the fluid droplets within the pump can be accelerated to a greater speed and may continue to collide with one another, further reducing droplet size. The pump can then expel the fluid droplets through the pump outlet. The pump outlet can be positioned such that the expelled fluid droplets from the pump interact with the fluid droplets expelled from the outlet of the housing. The two expelled fluid droplet streams can influence, collide, cross, interact, and/or disrupt each other. This interaction can cause the fluid droplets to further reduce in size and give them more velocity. This interaction can also generate a transitional flow that has properties of both a laminar flow and a turbulent flow. The fluid droplets can accelerate away from the pump and impact tissue of a patient or a membrane of a cell. This impact can also further reduce droplet size. As a result, the fluid droplets are capable of passing through the tissue. The fluid droplets can retain their native function as they pass through the tissue, thus administering the functional fluid droplets deep within a patient's tissue. Using both the piezoelectric transducer and the pump in combination can allow the fluid droplets to be significantly reduced in size, for example by a factor of about 10 or more, and accelerated at a high speed as the fluid droplets impact the tissue.

In some embodiments a fan, such as an axial fan (not shown), can be used in place of or in addition to the pump to generate turbulent flow. For example, the fan can be placed downstream of the pump so that fluid droplets exiting the pump can be drawn into the fan to create an additional turbulent environment and allow additional collisions between the fluid droplets prior to reaching the tissue. One skilled in the art will recognize that other such fluid disrupting elements could be used in place of or in addition to the pump to reduce fluid droplet size upon collision and to encourage further focusing of fluid mist that emerges.

Figure 12:
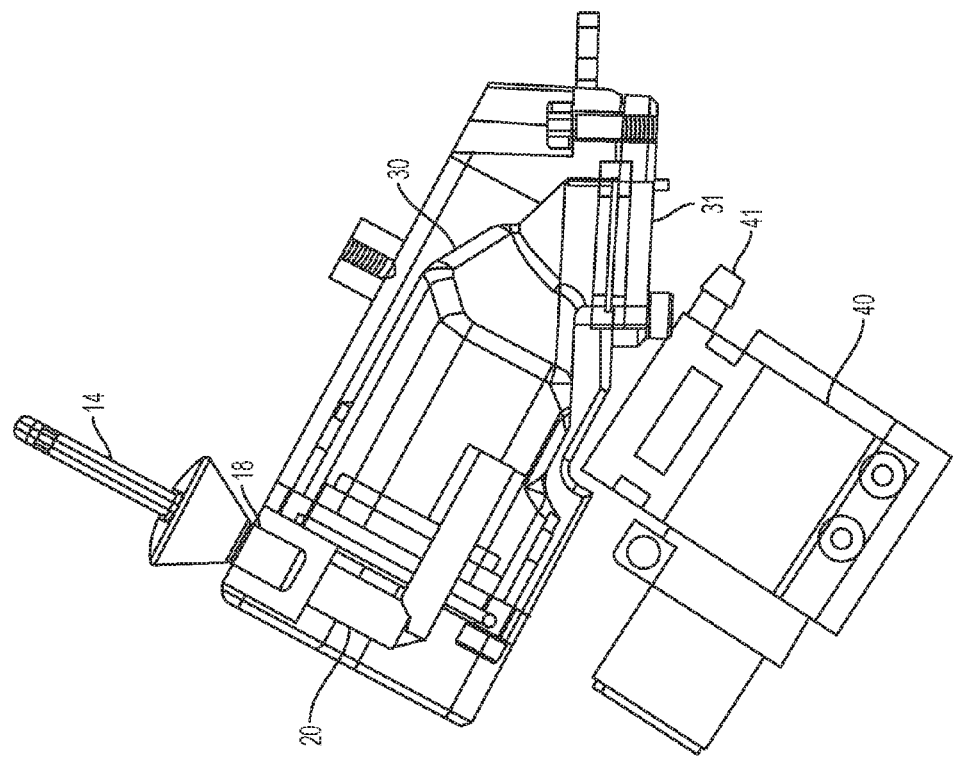
FIG. 12 is a partially transparent perspective view of the stopper, the reservoir, a piezoelectric transducer, and the pump of the fluid delivery device of FIG. 1.
Figure 11:
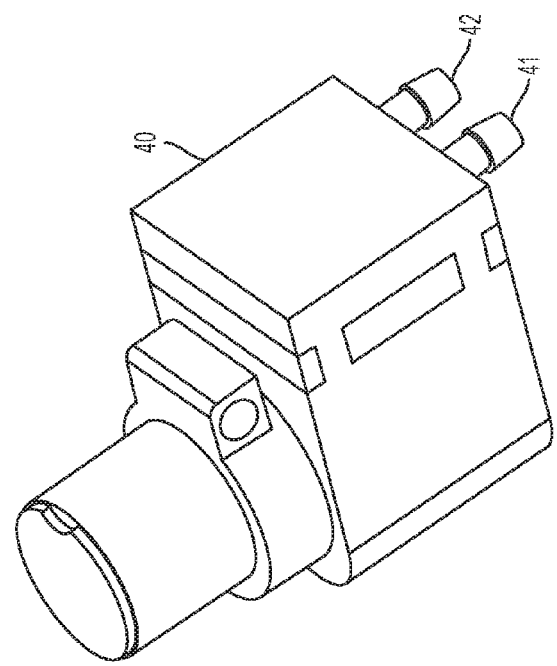
FIG. 11 is a perspective view of a pump of the fluid delivery device of FIG. 1.

As illustrated in FIGS. 11 and 12, the pump 40 is placed adjacent to the piezoelectric transducer 30. The pump 40 is in the form of a housing having an inner cavity formed therein. With reference to FIG. 6, a pump vibration jacket 43 can be disposed around the housing to reduce vibration of the pump 40. As further shown in FIGS. 11 and 12, the pump 40 includes a pump inlet 41 and a pump outlet 42 that are in fluid communication with the cavity in the pump 40, and that are positioned to influence the flow of fluid droplets from the piezo plate 31 and the outlet 16 of the housing 10. In particular, the illustrated pump inlet and pump outlet 41, 42 are positioned a distance apart from one another and have central axes that extend substantially parallel to one another. The pump inlet and pump outlet 41, 42 each extend from the pump 40 into the path of fluid flow exiting from the outlet 16 in the housing 10. The pump inlet and pump outlet 41, 42 together form an angle that is less than 90° with an axis of the outlet 16 of the housing 10, as illustrated in FIG. 12. In various embodiments, the angle between the pump inlet and pump outlet 41, 42 and the axis of the outlet 16 of the housing 10 can vary, for example between approximately 60° and approximately 90°, as long as the pump inlet and pump outlet 41, 42 can influence the flow of fluid droplets from the piezo plate 31 and the outlet 16 of the housing 10.

The configuration of the pump inlet and pump outlet 41, 42 can vary. In the illustrated embodiment, the pump inlet 41 is shaped as a cylindrical channel. In one embodiment, the pump inlet 41 has an inner diameter that is approximately 0.1 mm to approximately 10 cm. For example, the diameter can be approximately 1.5 mm. One skilled in the art will appreciate that the pump inlet 41 can be sized and/or shaped in any form necessary to operate with the pump and draw in fluid droplets. The illustrated pump outlet 42 is also shaped as a cylindrical channel, and the pump outlet 42 can likewise have a diameter that varies. In one embodiment, the diameter can be approximately 0.1 mm to approximately 10 cm. For example, the diameter can be approximately 1.5 mm. As with the pump inlet 41, the pump outlet 42 may vary in size and/or shape depending on the pump and the amount of fluid to be expelled.

The pump 40 can also have a variety of configurations to facilitate the flow of fluid therethrough. As shown in FIG. 11, the illustrated pump 40 is a pneumatic diaphragm pump. One non-limiting example of a diaphragm pump is the 3013VD/0,7/E/DC diaphragm pump provided by Thomas by Gardner Denver. In use, fluid droplets are accelerated within the pump 40. Altering a pump speed and/or a pressure of the pump 40 can influence the speed and/or size and/or expulsion direction of the fluid droplets. One skilled in the art will appreciate that the pump 40 may be any pump capable of reducing the size of fluid droplets and/or influencing the flow of fluid droplets from the piezoelectric transducer and/or the outlet of the housing, such as a rotary vane pump or a positive displacement pump.

The pump 40 is electrically coupled to the circuit board 50 and may be activated upon activation of the trigger 13. The pump speed and/or pump pressure may be varied manually or automatically. For example, the speed and/or pressure may be varied manually through use of a controller (not shown) either directly or wirelessly coupled to the circuit board 50 and capable of sending a signal to the control board 50 or automatically based on a signal from the cartridge 21. The controller can be the same controller for the piezoelectric transducer 30 or it can be a separate controller. The controller can take any form necessary to provide control over the pump speed and/or pump pressure, such as a dial, a knob, a panel, or a series of buttons positioned on the housing 10 or separately from the housing 10.

As indicated above, in use the pump 40 expels fluid droplets from the pump outlet 42. The direction and/or force of expulsion of the fluid droplets may be varied, for example by varying the pump speed and/or pump pressure. The fluid droplets will flow back into the spray output flowing from the outlet 16 in the housing, and the fluid spray output will pass through the tissue of the patient or into cells for delivery or transfection of molecules. The fluid may consist of any fluid with any molecular weight. It has been found that the combination of the piezoelectric transducer and the pump are effective to create a mist or stream of fluid having a size that will pass into tissue to a depth of, for example, 1 cm or deeper. As a result, fluid having a higher molecular weight can be utilized and will still penetrate into the tissue. In an exemplary embodiment, the fluid has a molecular weight of about 500 Daltons or greater. The molecular weight of the fluid may also be between about 500 Daltons and about 800 Daltons. The molecular weight may also be greater than 800 Daltons or less than 500 Daltons. After passing through the device 1, the resulting fluid droplets will be in the sub-micron range and can penetrate through skin pores (approximately 3 μm). A velocity and a width of a flow stream of the fluid droplets after expulsion may vary depending on the fluid used and the piezoelectric transducer and the pump and the size of the outlet, which can vary from about 0.1 to 5 cm in diameter. But the velocity may be, for example, 0.1 to 0.2 liters/sec, and the width of the spray output may be for example about 1 cm.

In certain exemplary embodiments, the fluid is a medicament used for treating wounds. For example, the fluid can be any antibiotic, for example an antibiotic to treat a skin and soft tissue infection such as ceftaroline. The functionality of the fluid, such as an antibiotic like ceftaroline, can be maintained as the fluid is converted into the fluid droplets and passed through the tissue of the patient. Additionally, while the device 1 can be used for a variety of transdermal delivery purposes, such as to treat skin and soft tissue infections, one skilled in the art will appreciate that fluid may be delivered to internal body tissue, e.g., via open surgical techniques, endoscopic techniques, or laparoscopic techniques. In other embodiments the device can be configured to delivery fluid intranasally. In various embodiments, the fluid can be a vaporized fluid configured for at least one of inhalation, oral delivery, ocular delivery, intra-aural delivery, rectal delivery, and vaginal delivery. The vaporized fluid can be configured for at least one of delivery into ears or eyes. The vaporized fluid can be delivered onto a plate, well, or other surface containing cells and/or cell layers and/or tissue layers and/or plant cell layers for delivery.

The fluid can be a cosmetically acceptable topical carrier. For example, the cosmetically acceptable topical carrier can include an ingredient selected from one or more of the following five classes: wetting agents, emulsifiers, emollients, humectants, and fragrances. In certain embodiments, the cosmetically acceptable topical carrier includes ingredients from two or more of the above-mentioned classes, such as ingredients from at least three or more of such classes. In some embodiments, the cosmetically acceptable topical carrier includes water, an emulsifier, and an emollient. Cosmetically acceptable topical carriers can also be solutions, suspensions, emulsions such as microemulsions and nanoemulsions, gels, solids and liposomes.

In some embodiments, the fluid can include an oil-water emulsion. The fluid can also include at least one of a DNA, protein, virus, phage, bacteria, RNA, mRNA, miRNA, aptamer, stabilized RNA, iRNA, siRNA, and a plasmid. The device and the fluid can also be configured to be used in CRISPR operations and/or applications, such as in gene editing and/or gene delivery.

As indicated above, the device 1 includes a circuit board. The circuit board can be coupled to the power source, the trigger, the pump, the cartridge, and/or the piezoelectric transducer. The circuit board can interact with the power source, the switch, the pump, the cartridge, and/or the piezoelectric transducer either directly or wirelessly. For example, the circuit board can be electrically coupled to the power source and can provide power to the pump and the piezoelectric transducer. The circuit board can receive signal (s) from the trigger, for example indicating actuation of the trigger by a user. The circuit board can send and receive signal(s) to and from the pump and the piezoelectric transducer. For example, the circuit board can send signals activating and/or deactivating the piezoelectric transducer and the pump. The circuit board can also send and receive signals regarding the functionality or condition of the piezoelectric transducer and the pump, such as the frequency of vibration and/or the voltage of the piezoelectric transducer and the pump speed and/or the pressure of the pump. The circuit board can additionally send signal(s) to and/or receive signal(s) from the cartridge, for example pertaining to instructions and details on fluid type, dosage information, dispersal rates, and dispersal times. The circuit board can then send signal(s) to and/or receive signal(s) from the pump and/or the piezoelectric transducer regarding the signal(s) sent to and/or received from the cartridge. Insertion of the cartridge and/or activation of the trigger may prompt signals from and/or to the circuit board, the pump, and/or the piezoelectric transducer. The circuit board may additionally send signals to and/or receive signals from a controller (not shown), for example relating to the operation and condition of the device. The controller may be the same controller or a different controller as the controllers that may control the functionality of the pump and the piezoelectric transducer. The circuit board can send signals or receive signals using integrated wireless technologies to external instruments or operators for adjustment of the dosage, the pump speed, the frequency of vibration and/or the voltage of the piezoelectric transducer, or for any other aspect of device operation with real time feedback.

As illustrated in FIGS. 4-6, the circuit board 50 is coupled between the power source 17 on the board's proximal end 50*p* and the piezoelectric transducer 30 and the pump 40 on the board's distal end 50*d*, with the trigger 13 coupled therebetween. However, one skilled in the art will appreciate that the circuit board 50 may be placed at any location within or on the housing 10 wherein the circuit board 50 can be coupled to the power source 17, the piezoelectric transducer 30, and the pump 40. Activation of the trigger 13 will cause the circuit board 50 to activate the piezoelectric transducer 30 and the pump 40, and deactivation of the trigger 13 will cause the circuit board 50 to deactivate the piezoelectric transducer 30 and the pump 40.

In some embodiments, activation of the trigger 13 can cause a pre-programmed response from the circuit board 50. For example, the cartridge 21 can be inserted into the device. Upon insertion, the cartridge 21 can send an instruction signal to the circuit board 50 containing dosage instructions regarding the fluid contained in the cartridge 21. Based on the instruction signal, the circuit board 50 can send signals to the pump 40 and the piezoelectric transducer 30 providing the appropriate pump-speed and frequency of vibration for the fluid to be administered. Upon activation of the trigger 13, the circuit board 50 can cause administration of the fluid according to the provided instruction signal. The circuit board 50 can also be configured to activate either just the piezoelectric transducer 30 or just the pump 40.

Figure 13:
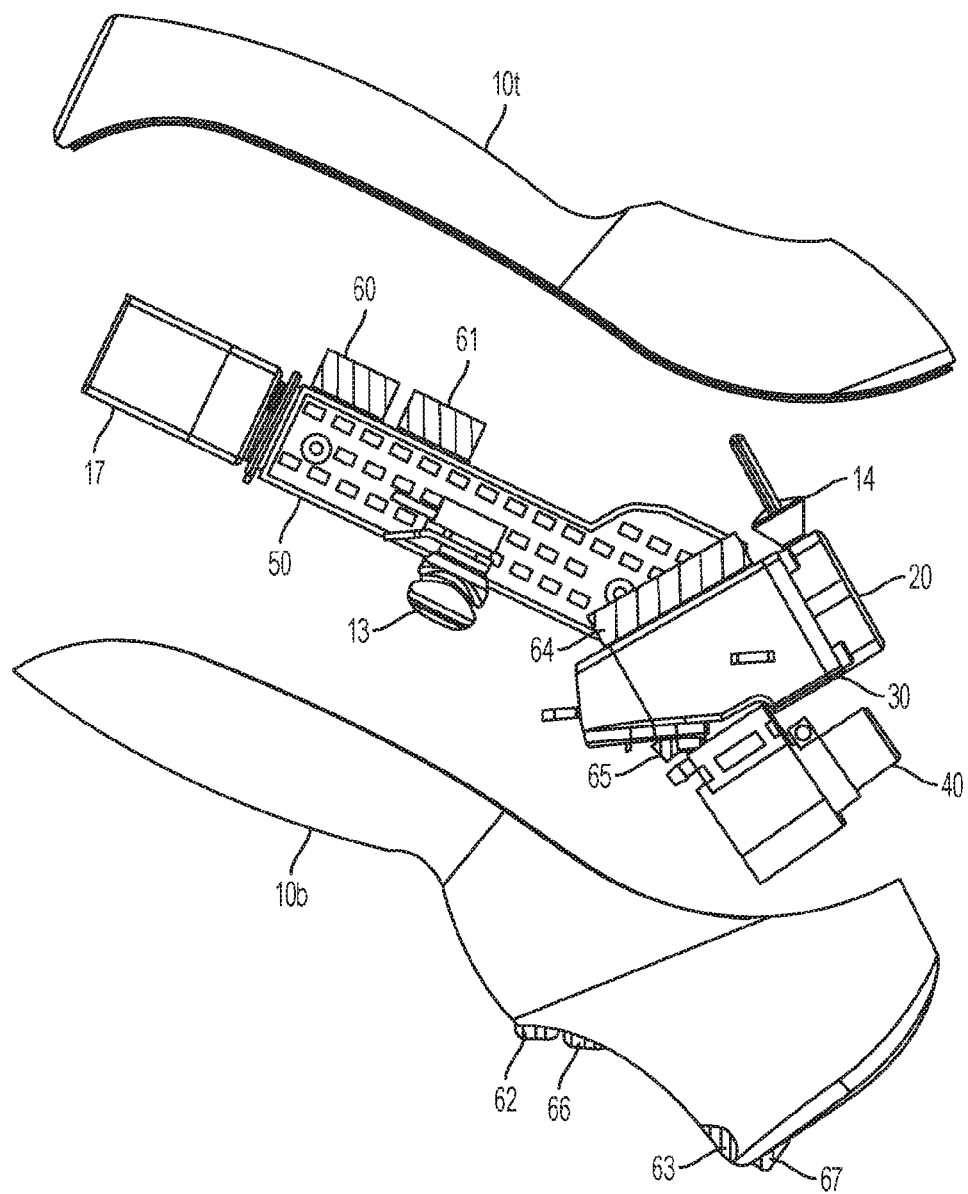
FIG. 13 is an exploded perspective view of internal and external components of the fluid delivery device of FIG. 1.

Additionally, the device may be further provided with sensors for detecting motion and/or orientation and/or distance of the device from tissue or other entity (such as cells on a plate or in wells). The sensors can send signals directly and/or wirelessly to the circuit board and/or a controller (not shown). The circuit board and/or controller may then alter functionality of the device based on the received signal(s). For example as illustrated in FIG. 13, a gyroscope 60 and an accelerometer 61 may be provided within or on the housing 10 for sending orientation signal(s) to the circuit board 50 and/or a separate controller to allow determination of an orientation of the device. The gyroscope 60 and the accelerometer 61 may be located anywhere within or on the housing 10. The circuit board 50 and/or controller may receive and use the orientation signal(s) by, for example, deactivating the device until the device is in a proper orientation for delivery of a fluid or altering the flow rate, pump-speed, and frequency of vibration based on the orientation of the device.

As another example, the device may include a distance sensor 62 positioned anywhere on the housing 10. The distance sensor may detect the distance of the device from a tissue of a patient and may send a distance signal(s) to the circuit board 50 and/or the controller. The circuit board 50 and/or controller may receive and use the distance signal(s) by deactivating the device until the device is within a proper range for delivery of a fluid. The distance sensor(s) can also be configured to interact with the cartridge.

Further components may be added to the device, such as a fan 63 coupled anywhere on the housing 10 and capable of drying tissue before, during, and/or after administration of the fluid drops. A cooling and/or heating system 64 may be provided within and/or on the housing 10 capable of heating and/or cooling the fluid and/or the tissue of the patient.

Ultraviolet (UV) light, white light, or a halogen may be provided to gel the fluid droplets after being expelled from the piezoelectric transducer 30, after being expelled from the pump 40, and/or after being expelled from the outlet 16. For example, a shutter and UV LED 65 can be coupled to the circuit board 50 and can expose the fluid droplets to UV light for variable durations as the fluid droplets are expelled from the pump 40 (as shown in FIG. 13). The shutter and UV LED may be placed anywhere within or on the housing 10. In another example, LED lights can be included to illuminate a target delivery site. Additionally, blue light or red light can be added for various purposes including increasing blood circulation to the site or for antibacterial use.

A controller for delivering electrical currents and/or acoustic and/or ultrasonic waves 66 may be coupled to the circuit board 50, positioned on the housing 10, and configured to pass current and/or waves from the device to the tissue of the patient to increase permeability. The controller can also include a timing feature, such as a timer that controls duration, pattern, length, etc. of delivery from the device, for example a timer for delivery over a given time period.

A camera 67 may be coupled to the circuit board 50 and placed anywhere on the housing 10 to allow a user to monitor a tissue treatment site and ensure a desired location on the tissue of the patient was treated while treatment is ongoing. The camera 67 can be configured to wirelessly transmit information to an external operator or device.

Figure 14:
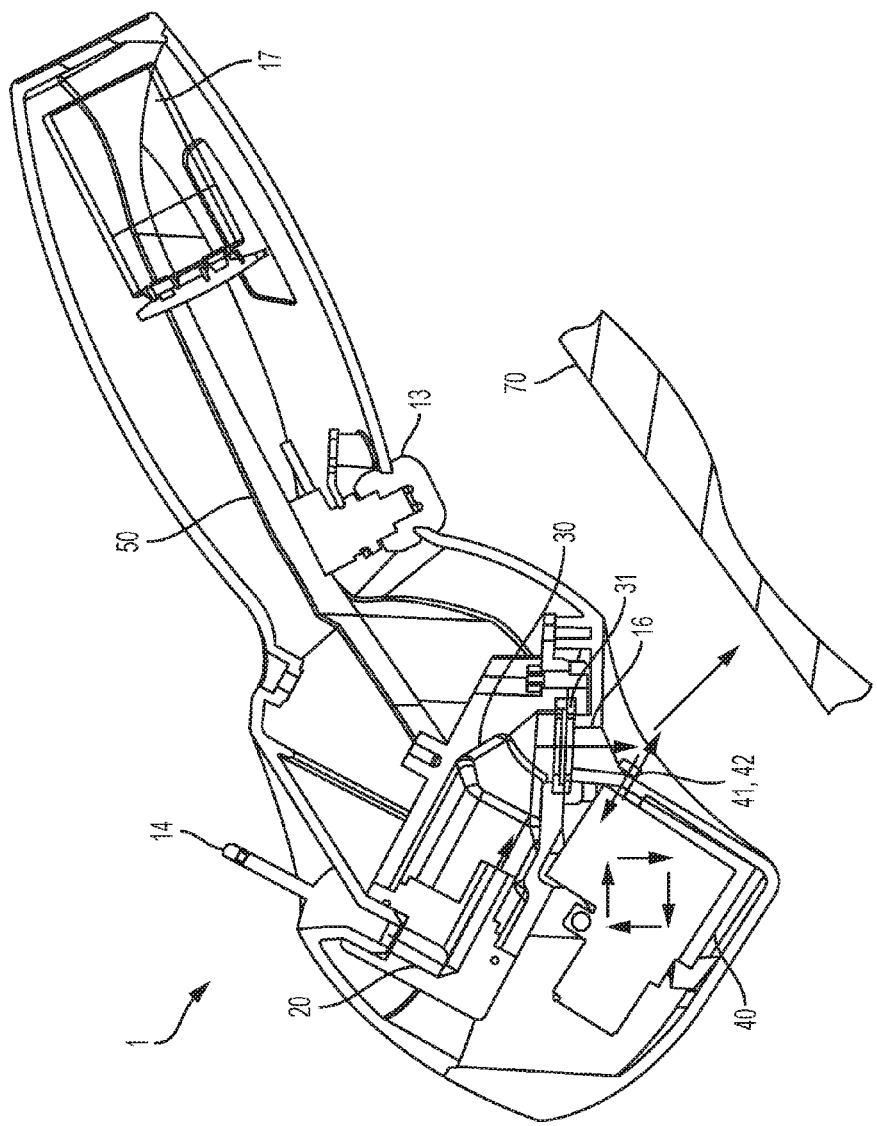
FIG. 14 is a cross-sectional view of the fluid delivery device of FIG. 1 showing a fluid flow path through the device.

In use, as illustrated in FIG. 14, a fluid is introduced into the reservoir 20 inside the housing 10. The fluid flows from the reservoir 20 and against the piezoelectric transducer 30 and piezo plate 31. The outlet 16 of the housing 10 may be positioned within a certain distance of a tissue 70 of a patient, and the device 1 need not contact tissue. The outlet 16 is also positioned to cause fluid to flow across the inlet 41 and the outlet 42 of the pump 40. Activating the switch 13 can cause the piezoelectric transducer 30 and/or the pump 40 to activate and can cause the fluid to be expelled as fluid droplets from the outlet 16 of the housing 10. The fluid expelled from the outlet 16 of the housing 10 will be drawn into the inlet 41 of the pump 40 and expelled from the outlet 42 into a path of the fluid droplets from the outlet 16 of the housing 10, causing the expelled fluid droplets to collide and further break apart. The fluid will penetrate into the tissue 70 of a patient, and due to the size of the particles the fluid can penetrate into the tissue by a depth of at least about 1 cm. The tissue 70 is used herein as an example delivery target, but a variety of delivery targets can be used, such as a layer of cells.

Provided herein are example test results, including real-world data obtained using a device as disclosed herein. The following examples should be considered to be illustrative and in no way limiting to the invention.

Example Test Results #1:

A device having a configuration as disclosed in FIGS. 1-14 was used in a test along with a standard aerosol generated using only the piezoelectric transducer to compare dye penetration between the device and the aerosol. A mix of water and brilliant blue dye with a molecular weight of 792 Daltons was used to test penetration. Both the aerosol and the device were held 1 cm away from skin, and the solution was sprayed onto chicken and porcine skin-covered tissue. The skin and tissue were cut and dye penetration was measured. It was shown that the spray from the aerosol did not penetrate either animal skin to any noticeable depth. However, using the device, a uniform penetration was observed to a depth of 1 cm for the porcine tissue and a depth of 1.23 cm for the chicken tissue, as shown in FIG. 15. These results show that drugs with a molecular weight of over 500 Daltons can be penetrated through skin and soft tissue using device. In between a range of 500 to 800 Daltons, there are a number of antibiotics, such as those used to treat skin and soft tissue infections. One example is ceftaroline, which is an antibiotic for Methicillin-resistant *Staphylococcus aureus*. As shown in FIG. 16, the molecular size of ceftaroline falls below the molecular size of the blue dye, while the topical aerosol is largely limited in its ability to deliver molecules with a molecular size greater than 500 Daltons to any noticeable depth. Thus the device can be successful at delivering ceftaroline to a significant depth within a tissue of a patient. In addition, although this test achieved penetration of large molecules deeper than 1 cm into tissue, this required depth can vary based on the nature of a skin condition or region of the body targeted. The method of delivery therefore can be designed to optimize depth of delivery based on clinical requirements.

Figure 17:
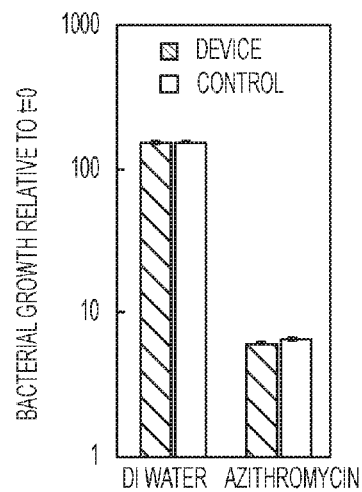
FIG. 17 is another graph showing bacterial growth using a fluid delivery device as disclosed herein.
Figure 18:
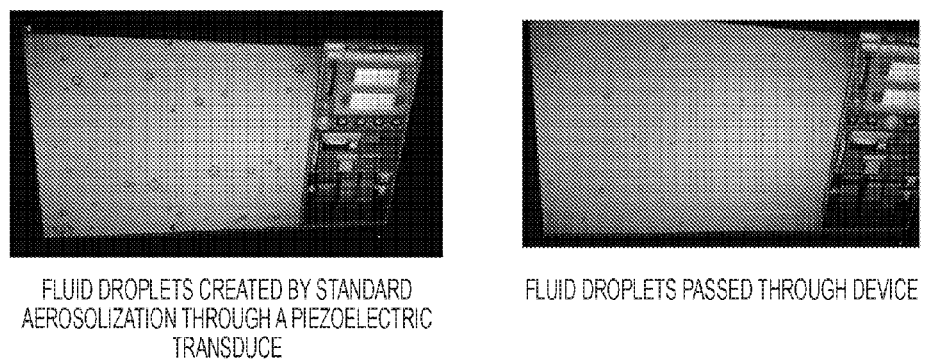
FIG. 18 is an image showing fluid droplets created by standard aerosolization as compared to fluid droplets created using a fluid delivery device as disclosed herein.
Figure 19:
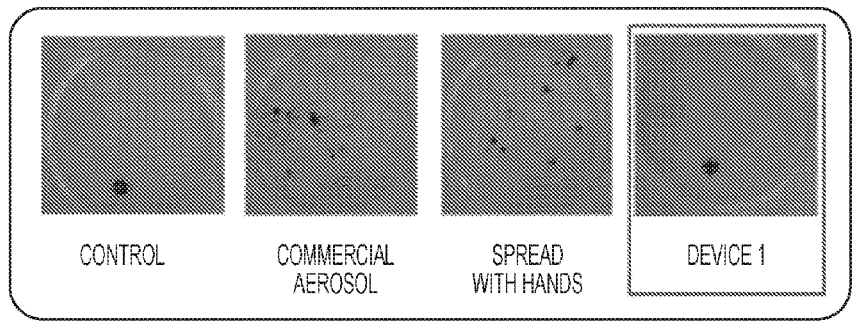
FIG. 19 is an image showing disruption of a droplet of food dye sitting in a bath of mineral oil by a commercial aerosol, a topical application with the human hand, and a fluid delivery device as disclosed herein.
Figure 20:
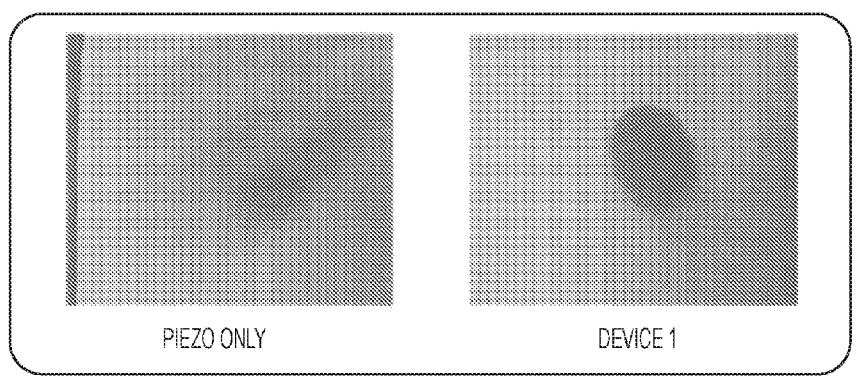
FIG. 20 is an image showing distribution of food dye after exiting a piezo versus exiting a fluid delivery device as disclosed herein.
Figure 21:
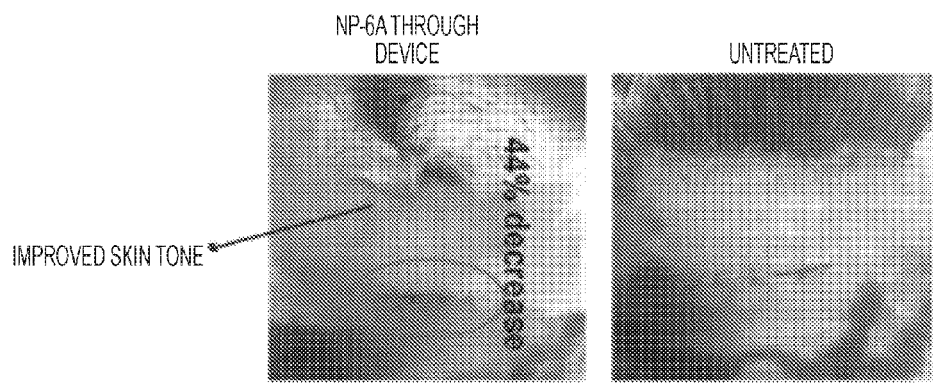
FIG. 21 is an image showing the results of delivering a peptide, NP-6A (780 DA), by a device similar to that disclosed herein into a lesion in a rat model compared to an untreated lesion.
Figure 22:
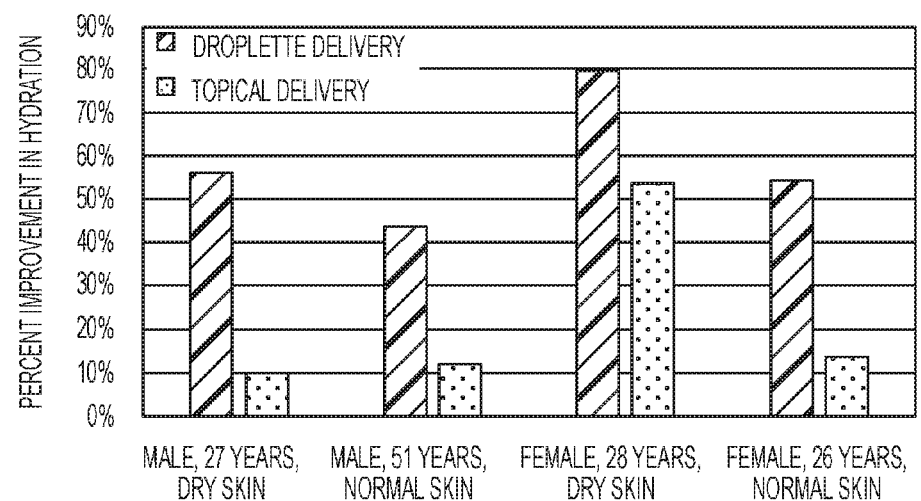
FIG. 22 is a graph showing measured hydration levels after water was delivered to 4 subjects through both topical delivery as compared to water delivered using a device similar to that disclosed herein.

Example Test Results #2:

In a further example, it was shown that antibiotics passing through a device having a configuration as disclosed in FIGS. 1-14 retained their native function against bacteria, as shown in FIG. 17. Inhibition of bacterial strain *E. Coli* DH5-α with antibiotics dissolved in deionized water was tested by passing the antibiotics and water through the device. The three antibiotics tested were azithromycin (5 mg/mL), vancomycin (15 mg/mL), and streptomycin (20 mg/mL). As a positive control, the same antibiotics (not passed through the device) were tested. Additional controls included deionized water, and deionized water passed through the device. After addition of 100 μl of antibiotics or deionized water into 8 mL of LB broth, 100 μl of bacterial stock at 0.5 OD at 600 nm was added. The experiment was performed with 4 biological replicates and 3 technical replicates, providing a sample size of n=12. Samples were incubated at 37° centigrade and 200 RPM in a shaker for 6 hours and then optical density was measured at 600 nm in a spectrophotometer. All antibiotics retained their native function after being passed through the device, and there was no decrease in bacterial inhibition due to passing through the device. Deionized water passed through the device had no antibacterial effects, indicating that the device itself does not induce bacterial inhibition. FIG. 17 shows the data for azithromycin with final ODs normalized relative to starting point ODs to display amount of growth over the time. Similarly, vancomycin and streptomycin retained their native function after being passed through the device.

Example Test Results #3:

In yet another experiment, the ability of a device having a configuration as disclosed in FIGS. 1-14 to enable deep penetration in comparison to a standard aerosol was explored. Water was fed into the reservoir of the device and collected either after standard aerosolization by the piezoelectric transducer alone or after passing through the device 1 with the pump in a bath containing light mineral oil (Sigma) with 1.5% (v/v) Span-80 (Sigma) as a stabilizer that would prevent droplet coalescence upon contact. The emulsions were then pipetted onto a coverglass and observed using brightfield microscopy under 4× magnification. As shown in FIG. 18, fluid droplets passed through the device with the pump were on average smaller by a factor of ten than those produced using standard aerosolization.

Example Test Results #4:

In another experiment, the ability of a device having a configuration as disclosed in FIGS. 1-14 to perform transdermal drug delivery was compared to a commercial aerosol designed to treat minor skin wounds and topical application with the human hand (such as in applying a lotion). The delivery methods were used to “disrupt” a droplet of food dye sitting in a bath of mineral oil. As is illustrated in FIG. 19, the only delivery method that left the droplet intact was the device while the commercial aerosol and spreading with hands distributed the food dye widely. In a similar experiment, the distribution of food dye was compared after exiting a piezo versus exiting the device. As illustrated in FIG. 20, the piezo led to uneven distribution while the device provided an even and more concentrated distribution over the area administered. The results of both studies suggest that the device provides significantly less force than existing approaches to transdermal delivery while being more even and uniform, suggesting that the device is well suited for transdermal drug delivery because the device is low pressure and causes little or no skin damage.

Example Test Results #5:

Another experiment was conducted to examine the results of delivering a wound-healing peptide. As illustrated in FIG. 21, a wound healing peptide, NP-6A (780 DA) was delivered by a device having a configuration as disclosed in FIGS. 1-14 into a lesion in a diabetic (ZDF) rat model. The peptide (in sterile saline) was delivered through the device at a concentration of 300 nM daily for 5 days. As visible in FIG. 21, the wound treated with the peptide showed much greater healing than the untreated wound, illustrating that functionality of the peptide was retained even after being delivered through the device. The experiment was repeated in healthy lean female rats (Zucker Lean) with a standardized skin punch where a 43% improvement was seen in rats treated with a peptide therapeutic delivered through the device. After 4 days of treatment, the untreated wound was an average of about 19.16 $mm^2$ in wound size (2.00 $mm^2$ STD) compared to an average of about 11.36 $mm^2$ wound size (2.77 mm2 STD) in rats treated with the peptide NP-6A delivered through the device. The results of the studies show that peptide drugs delivered through the device retain their pharmacological functionality, delivery through the device causes no or very minimal skin disruption, which is crucial for treatment exemption, and that large drugs can be effectively delivered into skin through the device, for example by safely delivering large peptides into wounds.

Example Test Results #6:

In yet another experiment, 4 human subjects volunteered to have about 50 μL of sterile distilled water sprayed into their hand and have hydration levels measured with a Corneometer CM825 device. Skin was visually inspected for any discoloration at the time of study and after 24 hours, and subject comfort was assessed and self-reported. A pen was used to draw circles denoting a delivery site (having a circle diameter of about 1.5 cm) on the backs of the right and left hands. Hydration in the circled regions for both the right and left hands was assessed at the start with a Corneometer CM 825. A device having a configuration as disclosed in FIGS. 1-14 was used for about 30 seconds to deliver about 50 μL sterile water to the left hand of each subject. After about 5 seconds of rest, the hand was blotted dry with a tissue. About 100 μL of sterile water was topically applied to the back of the right hand of each subject in the circled region and spread to cover that area. After about 5 seconds of rest, that hand was blotted dry with a tissue. As illustrated in FIG. 22, the Corneometer CM 825 was used to assess and record hydration after delivery for both hands. No subjects reported any discomfort or discoloration when experiencing the device at the time of delivery or after a 24 hour follow-up. Subjects described delivery through the device as feeling like a slightly cool mist. After 1 hour and after 2 hours, Subject 3 was reassessed with the Corneometer CM 825, and the results are illustrated in TABLE 1 below.

TABLE 1

| Time and Activity | Droplette Hydration | Topical Hydration |
|---|---|---|
| 1 Hour: Resting | 58% improvement over starting hydration | 0% improvement (back to hydration at start) |
| 2 Hours: Had eaten lunch and consumed 2 cups of water | 55% improvement over starting hydration (we assume some part is due to food and water consumption) | 11% improvement over baseline (we assume this is due to food and water consumption) |

Results from these studies demonstrate that significantly more water was delivered into both young (26 year old) and mature (51 year old) skin when using the device compared to topical application. Additionally, the follow-up with Subject 3 indicated that, once water is delivered using the device, the water remains localized to that site and is not quickly evaporated away compared to topical delivery.

Figure 23:
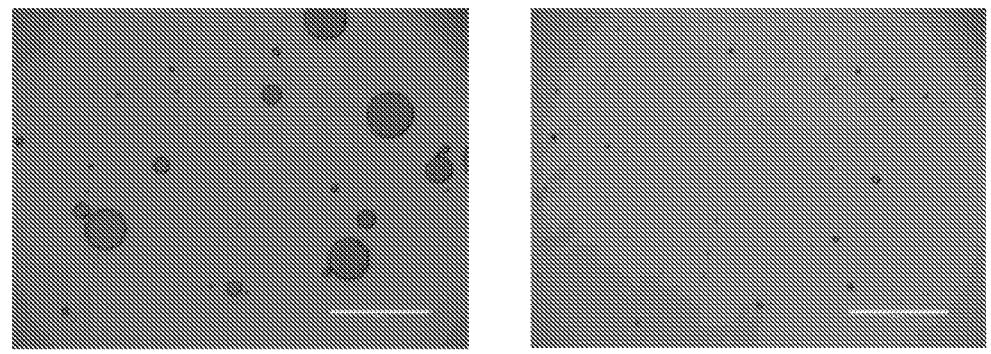
FIG. 23 is an image of fluid droplets expelled from a device similar to that disclosed herein and a standard aerosol.

Analysis of the experiments elucidates a probable mechanism for fluid droplet behavior in the device. Fluid droplets are ejected from the device in a turbulent regime with a high Weber number. The Weber number compares the effect of inertia to surface tension resulting in a high Weber number meaning that inertial forces dominate relative to surface tension and dictate behavior of fluid droplet collision. Fluids that come into contact with the device can be sucked into the pump where they undergo droplet breakup because of this fluid regime, rather than forming into a single stream or a jet. The droplet breakup inside of the pump leads to formation of significantly smaller fluid droplets that also have higher velocity and can penetrate into skin rather than forming a pool on the surface of the skin. As illustrated in FIG. 23, data supports this understanding. Fluid droplets that emerge from the device are significantly smaller than those formed just using an aerosol of a piezoelectric crystal and retain velocity and elasticity, allowing fluid droplets from the device to penetrate skin and soft tissue.

Calculation of Weber Number:

The Weber number is a dimensionless number that compares the relative effect of inertial forces to surface tension forces. At higher Weber numbers, fluid droplet formation and breakup is the prominent mechanism that determines fluid droplet size and distributions.

Inertial forces will scale as approximately $\rho U^2 l^2$, while surface forces will scale as approximately $\sigma l$. $\rho$ is the density of the fluid (kg/m$^3$). U is velocity (m/s). l is the characteristic length (typically the fluid droplet diameter) (m). $\sigma$ is the surface tension (N/m).

Typically the length scale over which inertia and surface tension act on fluid droplets is the same, so the Weber number may be written as (and the ratio comes out as):

$$We = \frac{\rho U^2 l}{\sigma}$$

Determination of the Weber number herein considered water being aerosolized through a pressurized system at room temperature with the following experimental parameters:

$\rho$=approximately 1000 kg/m$^3$
U=approximately 3.75 m/s
l=approximately 50E-5 m
$\sigma$=approximately 0.072 kg/s$^2$ A fluid droplet size can vary between 1 and 1000 µm.

Based on these parameters, a Weber number herein is estimated to be about 10 to 100, resulting in a regime where there should be significant fluid droplet break up upon collision. For there to be droplet breakup, the Weber number should at least exceed 1 because inertia will then dominate over surface tension. It is estimated that a Weber number of between 10 and 50 will provide the focusing and droplet breakup effects sufficient to enhance penetration of molecules into tissue or cells.

Example Test Results #7

Figure 24:
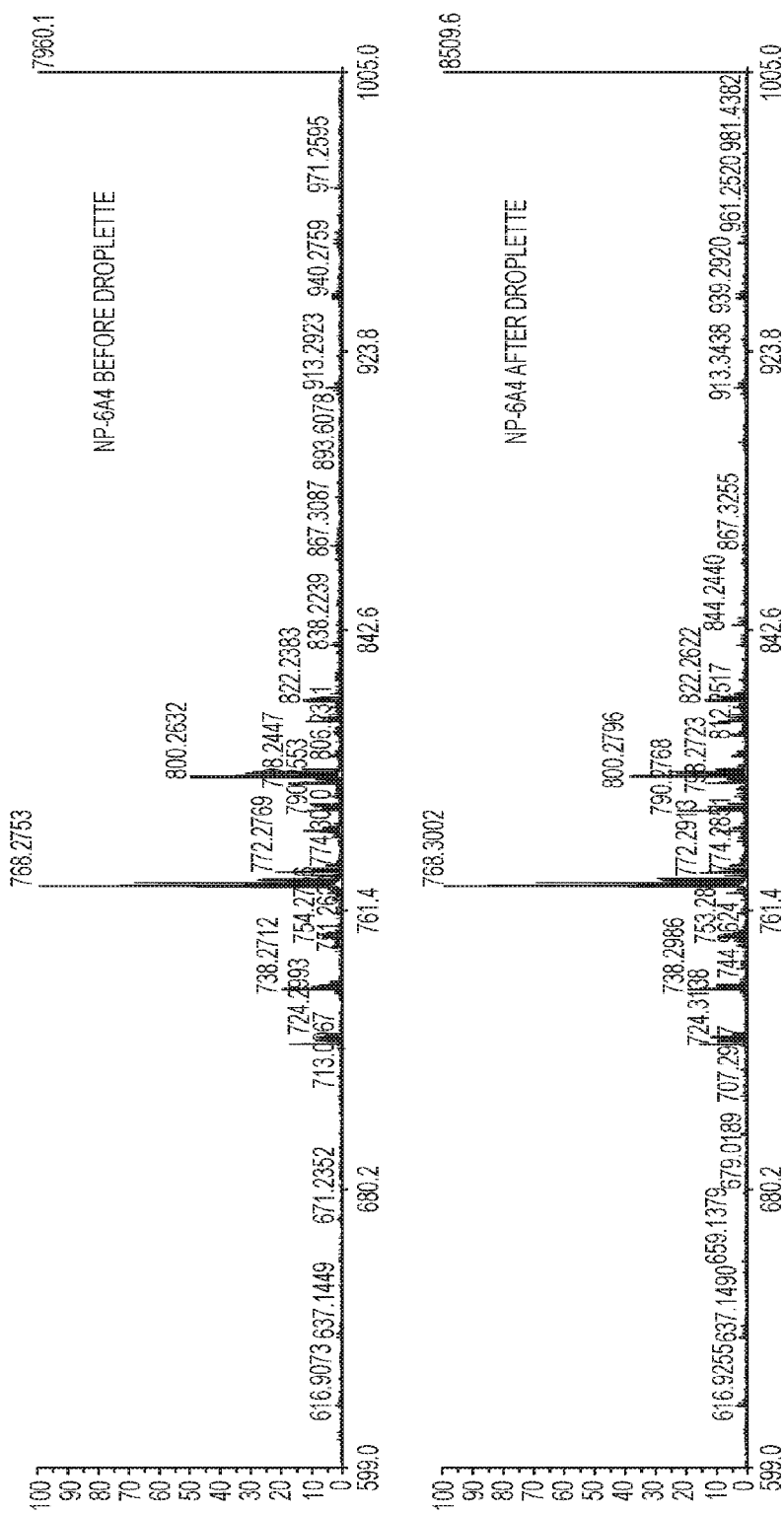
FIG. 24 is a mass spectrometry trace of a peptide before and after being passed through a device similar to that disclosed herein.

In another experiment, it was verified that peptides that pass through a device having a configuration as disclosed in FIGS. 1-14 do not get broken up or damaged. NP-6A solution (768.3 Da) before and after passing through the device were subjected to MALDI TOF-TOF MS Analysis. MS spectra of samples were acquired over a mass range of 700 to 1000 m/z (with a "focus mass of 800 m/z). MS spectra, 5000 laser shots, were summed sub-spectra (50 laser shots×100 across the sample). As illustrated in FIG. 24, MALDI-TOF MS spectra of samples showed that the most abundant peptide peak in NP-6A solution before and after passing through the device was 768.3 Da indicating that the device does not induce any significant degradation of the peptide.

Example Test Results #8

Figure 25:
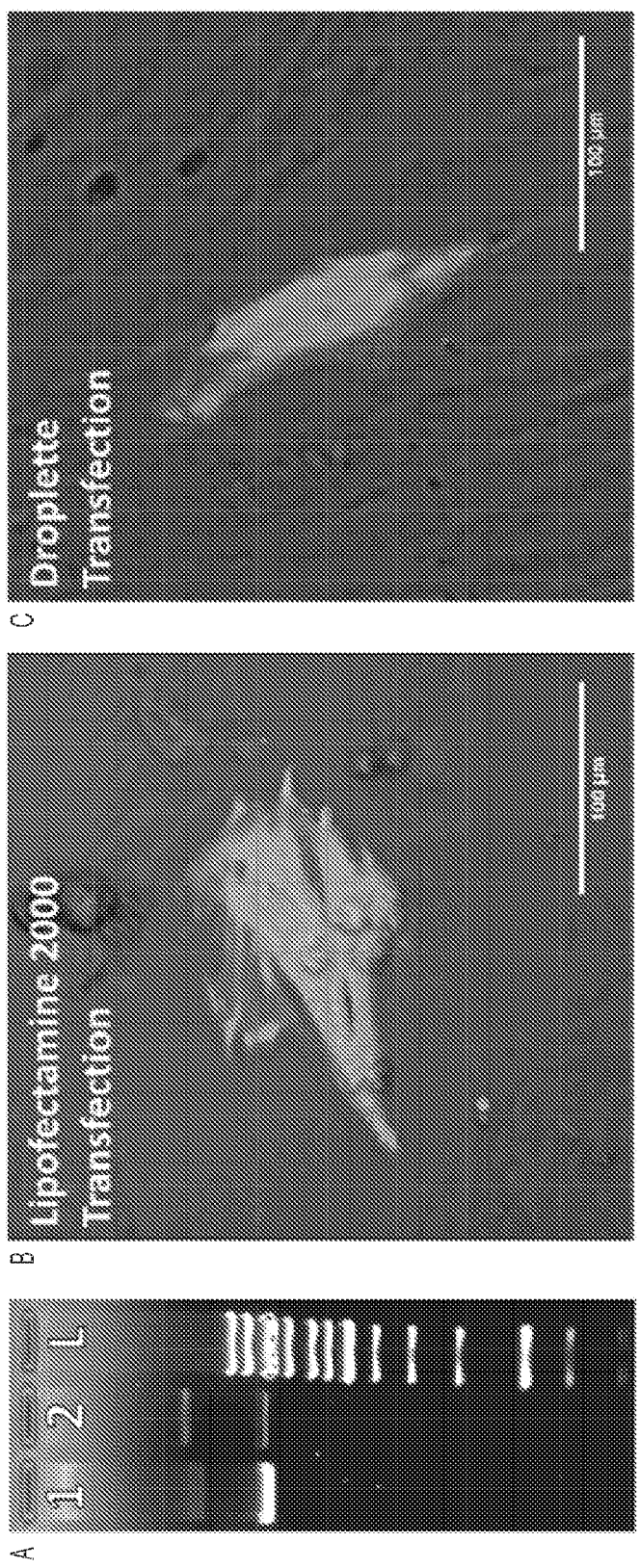
FIG. 25 is an image of an agarose gel showing GFP plasmid and H9C2 cells into which GFP plasmid was delivered using a device similar to that disclosed herein and compared with a commercially available chemical transfection reagent (Lipofectamine 2000).

In another experiment, p-MIR-GFP vector in aqueous solution (10 µg in 500 µl, 3400 kDa in size) was delivered using a device having a configuration as disclosed in FIGS. 1-14 onto a monolayer of H9C2 cells, and green fluorescent signal was detected after 72 hours of incubation using a Leica DMI4000B inverted microscope using a CCD camera. Compared to delivery using a commercially available chemical transfection reagent, lipofectamine, the device delivery resulted in less cell toxicity and comparable delivery efficiency, as illustrated in FIG. 25.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. One skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A fluid delivery device, comprising:
a housing, a fluid vaporizer disposed within the housing and configured to receive fluid and to produce an aerosol mist of liquid particles from the fluid, and a pump configured to accelerate the aerosol mist produced by the fluid vaporizer, wherein the pump has an inlet port positioned to disrupt a flow path of the aerosol mist produced by the fluid vaporizer such that the aerosol mist can be drawn into the pump through the inlet port, and the pump has an outlet port for expelling the aerosol mist therefrom.

2. The device of claim 1, wherein the fluid vaporizer comprises a piezoelectric transducer.

3. The device of claim 1, wherein the pump is configured to reduce a size of the liquid particles produced by the fluid vaporizer.

4. The device of claim 1, wherein the pump is configured to reduce a size on average of the liquid particles produced by the fluid vaporizer by a factor of about 10.

5. The device of claim 1, wherein the housing has a fluid-retaining reservoir and the fluid vaporizer is configured to receive fluid from the reservoir.

6. The device of claim 1, wherein the fluid vaporizer and the pump are configured to generate an aerosol mist that can pass into up to 1 cm of tissue when an outlet on the housing through which the aerosol mist passes is positioned about 1 cm away from the tissue.

7. The device of claim 1, wherein the aerosol mist is configured to pass into the surface on a timescale of between 1 microsecond and 600 seconds.

8. The device of claim 1, wherein the housing has an outlet formed therein and positioned such that the fluid vaporizer can eject the aerosol mist from the housing through the outlet.

9. The device of claim 8, wherein the pump is configured to draw in and accelerate the aerosol mist after the aerosol mist passes through the outlet in the housing.

10. The device of claim 8, wherein the pump includes a fluid inlet port and a fluid outlet port, the fluid inlet and outlet ports being positioned adjacent to the outlet in the housing.

11. The device of claim 10, wherein the fluid inlet and outlet ports of the pump extend substantially parallel to one another and extend transverse to a central longitudinal axis of the outlet in the housing.

12. The device of claim 1, wherein the pump comprises a diaphragm pump.

13. The device of claim 1, wherein the pump includes an axial fan.

14. The device of claim 1, wherein the housing includes an activation switch electronically coupled to the fluid vaporizer and the pump.

15. The device of claim 14, wherein the housing includes a power source for providing power to the fluid vaporizer and the pump.

16. The device of claim 1, further comprising a cartridge removably matable to the housing and configured to deliver fluid to the housing.

17. The device of claim 16, wherein the cartridge is configured to provide at least one of a dosage instruction or timing instructions to the device including a selected pump-speed of the pump and a selected frequency of vibration of the fluid vaporizer for the fluid.

18. The device of claim 16, wherein the device is configured to be inoperable unless the cartridge is mated to the housing.

19. The device of claim 17, wherein the housing includes an activation switch that is electronically coupled to the fluid vaporizer and the pump and that is configured to simultaneously activate the fluid vaporizer and the pump according to the dosage instruction of the cartridge.

20. The device of claim 1, further comprising a controller disposed on the housing and configured to alter a frequency of the fluid vaporizer and at least one of a pump-speed of the pump and a duration of device operation.

21. The device of claim 1, further comprising a sensor disposed on the housing and configured to determine a distance from the device to a skin of a patient.

22. The device of claim 1, further comprising a fluid that includes at least one of a DNA, protein, virus, phage, bacteria, RNA, mRNA, miRNA, aptamer, stabilized RNA, iRNA, siRNA, chemicals, small molecules, and a plasmid.

23. The device of claim 1, further comprising a vaporized fluid configured for at least one of inhalation, ocular delivery, intra-aural delivery, rectal delivery, oral delivery, and vaginal delivery.

24. The device of claim 1, further comprising a vaporized fluid configured for at least one of intra-cellular, intra-nuclear, intra-tissue delivery, intra-plant delivery, polymeric delivery, and protein-structure delivery.

25. A fluid delivery device, comprising:
a housing;
a fluid-retaining reservoir in the housing;
a piezoelectric transducer disposed within the housing and configured to receive fluid from the reservoir and to produce an aerosol mist of liquid particles from the fluid, the housing having an outlet formed therein and positioned such that the piezoelectric transducer can eject the aerosol mist from the housing through the outlet; and
a pump having an inlet and an outlet positioned adjacent to the outlet of the housing, the inlet port configured to draw into the pump the aerosol mist ejected from the outlet in the housing, and the outlet port configured to expel the aerosol mist therefrom into a path of the aerosol mist ejected from the housing by the piezoelectric transducer.

* * * * *